(12) United States Patent
Craig et al.

(10) Patent No.: US 8,647,426 B2
(45) Date of Patent: Feb. 11, 2014

(54) DENTAL FILLER AND METHODS

(75) Inventors: Bradley D. Craig, Cottage Grove, MN (US); Gregory A. Kobussen, Woodbury, MN (US)

(73) Assignee: 3M Innovative Properties Company, St. Paul, MN (US)

(*) Notice: Subject to any disclaimer, the term of this patent is extended or adjusted under 35 U.S.C. 154(b) by 906 days.

(21) Appl. No.: 12/519,393

(22) PCT Filed: Dec. 28, 2007

(86) PCT No.: PCT/US2007/089045
§ 371 (c)(1),
(2), (4) Date: Jun. 16, 2009

(87) PCT Pub. No.: WO2008/083275
PCT Pub. Date: Jul. 10, 2008

(65) Prior Publication Data
US 2010/0089286 A1    Apr. 15, 2010

Related U.S. Application Data

(60) Provisional application No. 60/877,526, filed on Dec. 28, 2006.

(51) Int. Cl.
*C09K 3/00* (2006.01)
*C04B 14/00* (2006.01)
*C04B 14/04* (2006.01)

(52) U.S. Cl.
USPC .............................. 106/35; 106/401; 106/491

(58) Field of Classification Search
USPC .................................. 106/401, 405, 35, 491
See application file for complete search history.

(56) References Cited

U.S. PATENT DOCUMENTS

| | | | |
|---|---|---|---|
| 2,984,628 | A | 5/1961 | Alexander |
| 3,018,262 | A | 1/1962 | Schroeder |
| 3,066,112 | A | 11/1962 | Bowen |
| 3,117,099 | A | 1/1964 | Proops |
| 3,442,817 | A | 5/1969 | Luebke |
| 3,514,252 | A | 5/1970 | Levy |
| 3,539,533 | A | 11/1970 | Lee |
| 3,577,515 | A | 5/1971 | Vandegaer |
| 3,629,187 | A | 12/1971 | Waller |
| 3,691,140 | A | 9/1972 | Silver |

(Continued)

FOREIGN PATENT DOCUMENTS

| | | |
|---|---|---|
| CN | 1188640 | 7/1998 |
| CN | 1212865 | 4/1999 |

(Continued)

OTHER PUBLICATIONS

Adamson, "Aminoalkyl Tertiary Carbinols and Derived Products", *Journal of the Chemical Society*, 1949, Part 1, pp. 144-152.

(Continued)

*Primary Examiner* — Shuangyi Abu Ali
(74) *Attorney, Agent, or Firm* — Nicole J. Einerson

(57) ABSTRACT

A dental filler is disclosed. The filler is produced by admixing a metal oxide sol and a water-soluble organic binder; drying said mixed sol into a dried product; and calcining said dried product; wherein said filler is a substantially amorphous cluster. The filler can be mixed into a hardenable resin to provide radiopaque dental materials having desirable strength and aesthetic character.

12 Claims, 1 Drawing Sheet

(56) References Cited

U.S. PATENT DOCUMENTS

| | | |
|---|---|---|
| 3,708,296 A | 1/1973 | Schlesinger |
| 3,709,706 A | 1/1973 | Sowman |
| 3,709,866 A | 1/1973 | Waller |
| 3,729,313 A | 4/1973 | Smith |
| 3,741,769 A | 6/1973 | Smith |
| 3,751,399 A | 8/1973 | Lee |
| 3,766,132 A | 10/1973 | Lee |
| 3,793,041 A | 2/1974 | Sowman |
| 3,808,006 A | 4/1974 | Smith |
| 3,860,556 A | 1/1975 | Taylor |
| 3,893,840 A | 7/1975 | Wason |
| 4,002,669 A | 1/1977 | Gross |
| 4,069,055 A | 1/1978 | Crivello |
| 4,071,424 A | 1/1978 | Dart |
| 4,115,346 A | 9/1978 | Gross |
| 4,122,160 A | 10/1978 | Wason |
| 4,141,144 A | 2/1979 | Lustgarten |
| 4,158,641 A | 6/1979 | Miyai |
| 4,216,288 A | 8/1980 | Crivello |
| 4,250,053 A | 2/1981 | Smith |
| 4,250,311 A | 2/1981 | Crivello |
| 4,259,075 A | 3/1981 | Yamauchi |
| 4,259,117 A | 3/1981 | Yamauchi |
| 4,267,097 A | 5/1981 | Michl |
| 4,292,029 A | 9/1981 | Craig |
| 4,298,738 A | 11/1981 | Lechtken |
| 4,308,190 A | 12/1981 | Walkowiak |
| 4,324,744 A | 4/1982 | Lechtken |
| 4,327,014 A | 4/1982 | Kawahara |
| 4,356,296 A | 10/1982 | Griffith |
| 4,379,695 A | 4/1983 | Orlowski |
| 4,385,109 A | 5/1983 | Lechtken |
| 4,387,240 A | 6/1983 | Berg |
| 4,389,497 A | 6/1983 | Schmitt |
| 4,394,403 A | 7/1983 | Smith |
| 4,402,856 A | 9/1983 | Schnoring |
| 4,404,150 A | 9/1983 | Tsunekawa |
| 4,427,799 A | 1/1984 | Orlowski |
| 4,487,759 A | 12/1984 | Nesbitt |
| 4,490,179 A | 12/1984 | Bernhard |
| 4,499,251 A | 2/1985 | Omura |
| 4,503,169 A | 3/1985 | Randklev |
| 4,532,123 A | 7/1985 | Gardner |
| 4,537,940 A | 8/1985 | Omura |
| 4,539,382 A | 9/1985 | Omura |
| 4,544,359 A | 10/1985 | Waknine |
| 4,545,924 A | 10/1985 | Ritter |
| 4,567,030 A | 1/1986 | Yuasa |
| 4,612,138 A | 9/1986 | Keiser |
| 4,617,327 A | 10/1986 | Podszun |
| 4,619,817 A | 10/1986 | Stambaugh |
| 4,629,746 A | 12/1986 | Michl |
| 4,642,126 A | 2/1987 | Zador |
| 4,648,843 A | 3/1987 | Mitra |
| 4,649,165 A | 3/1987 | Kuhlmann |
| 4,652,274 A | 3/1987 | Boettcher |
| 4,661,540 A | 4/1987 | Le |
| 4,665,217 A | 5/1987 | Reiners |
| 4,689,293 A | 8/1987 | Goosen |
| 4,696,955 A | 9/1987 | Kuhlmann |
| 4,701,326 A | 10/1987 | Nelsen |
| 4,708,861 A | 11/1987 | Popescu |
| 4,710,523 A | 12/1987 | Lechtken |
| 4,719,091 A | 1/1988 | Wusirika |
| 4,737,593 A | 4/1988 | Ellrich |
| 4,746,513 A | 5/1988 | Smith |
| 4,746,685 A | 5/1988 | Masuhara |
| 4,755,377 A | 7/1988 | Steer |
| 4,769,351 A | 9/1988 | Soumiya |
| 4,772,436 A | 9/1988 | Tyszblat |
| 4,772,511 A | 9/1988 | Wood |
| 4,772,530 A | 9/1988 | Gottschalk |
| 4,778,671 A | 10/1988 | Wusirika |
| 4,784,794 A | 11/1988 | Kato |
| 4,868,288 A | 9/1989 | Meier |
| 4,872,936 A | 10/1989 | Engelbrecht |
| 4,874,450 A | 10/1989 | Gottschalk |
| 4,886,624 A | 12/1989 | Gradeff |
| 4,911,928 A | 3/1990 | Wallach |
| 4,923,905 A | 5/1990 | Masuhara |
| 4,927,560 A | 5/1990 | Osaka |
| 4,931,414 A | 6/1990 | Wood |
| 4,946,665 A | 8/1990 | Recasens |
| 4,954,414 A | 9/1990 | Adair |
| 4,985,229 A | 1/1991 | Obitsu |
| 4,985,340 A | 1/1991 | Palazzotto et al. |
| 5,009,597 A | 4/1991 | Schaefer |
| 5,037,579 A | 8/1991 | Matchett |
| 5,045,569 A | 9/1991 | Delgado |
| 5,055,372 A | 10/1991 | Shanklin |
| 5,057,393 A | 10/1991 | Shanklin |
| 5,073,476 A | 12/1991 | Meier |
| 5,076,844 A | 12/1991 | Fock |
| 5,084,586 A | 1/1992 | Farooq |
| 5,089,536 A | 2/1992 | Palazzotto |
| 5,089,606 A | 2/1992 | Cole |
| 5,124,417 A | 6/1992 | Farooq |
| 5,130,347 A | 7/1992 | Mitra |
| 5,154,762 A | 10/1992 | Mitra |
| 5,190,583 A | 3/1993 | Menzel |
| 5,219,899 A | 6/1993 | Panster |
| 5,234,870 A | 8/1993 | Osaka |
| 5,248,706 A | 9/1993 | Panster |
| 5,275,759 A | 1/1994 | Osaka |
| 5,332,429 A | 7/1994 | Mitra |
| 5,350,782 A | 9/1994 | Sasaki |
| 5,432,130 A | 7/1995 | Rheinberger |
| 5,460,701 A | 10/1995 | Parker |
| 5,470,910 A | 11/1995 | Spanhel |
| 5,501,727 A | 3/1996 | Wang |
| 5,508,313 A | 4/1996 | Delgado |
| 5,530,038 A | 6/1996 | Yamamoto |
| 5,545,423 A | 8/1996 | Soon-Shiong |
| 5,545,676 A | 8/1996 | Palazzotto |
| 5,558,849 A | 9/1996 | Sharp |
| 5,593,781 A | 1/1997 | Nass |
| 5,609,675 A | 3/1997 | Noritake |
| 5,618,763 A | 4/1997 | Frank |
| 5,628,806 A | 5/1997 | Celikkaya |
| 5,643,497 A | 7/1997 | Kaga |
| 5,645,844 A | 7/1997 | Henderson |
| 5,648,407 A | 7/1997 | Goetz |
| 5,658,376 A | 8/1997 | Noguchi |
| 5,694,701 A | 12/1997 | Huelsman |
| 5,698,483 A | 12/1997 | Ong |
| 5,713,994 A | 2/1998 | Kramer |
| 5,760,126 A | 6/1998 | Engle |
| 5,776,239 A | 7/1998 | Bruno |
| 5,830,242 A | 11/1998 | Yao |
| 5,856,373 A | 1/1999 | Kaisaki |
| 5,869,548 A * | 2/1999 | Ikushima et al. ............. 523/116 |
| 5,879,715 A | 3/1999 | Higgins |
| 5,886,069 A | 3/1999 | Bolt |
| 5,914,185 A * | 6/1999 | Shoher et al. ................. 428/323 |
| 5,935,275 A | 8/1999 | Burgard |
| 5,936,006 A | 8/1999 | Rheinberger |
| 5,942,559 A | 8/1999 | Voser |
| 5,962,550 A | 10/1999 | Akahane |
| 5,980,697 A | 11/1999 | Kolb |
| 5,998,495 A | 12/1999 | Oxman |
| 6,020,395 A | 2/2000 | Angeletakis |
| 6,025,406 A | 2/2000 | Oxman |
| 6,030,606 A | 2/2000 | Holmes |
| 6,063,830 A | 5/2000 | Deguchi |
| 6,121,344 A | 9/2000 | Angeletakis |
| 6,136,881 A | 10/2000 | Sekiguchi |
| 6,136,886 A | 10/2000 | Deguchi |
| 6,232,367 B1 | 5/2001 | Kobashigawa |
| 6,251,963 B1 | 6/2001 | Kohler |
| 6,281,271 B1 | 8/2001 | Rumphorst |
| 6,306,926 B1 | 10/2001 | Bretscher |
| 6,376,590 B2 | 4/2002 | Kolb |
| 6,387,981 B1 | 5/2002 | Zhang |
| 6,482,284 B1 | 11/2002 | Reidt |

(56) References Cited

U.S. PATENT DOCUMENTS

| | | | |
|---|---|---|---|
| 6,565,973 | B2 | 5/2003 | Duff |
| 6,572,693 | B1 | 6/2003 | Wu |
| 6,579,919 | B2 | 6/2003 | Konings |
| 6,627,327 | B2 | 9/2003 | Reid et al. |
| 6,632,528 | B1 * | 10/2003 | Clough ................. 428/402 |
| 6,648,645 | B1 * | 11/2003 | MacDougald et al. ....... 433/223 |
| 6,648,957 | B1 | 11/2003 | Andes |
| 6,730,156 | B1 * | 5/2004 | Windisch et al. ............... 106/35 |
| 6,740,267 | B1 | 5/2004 | Sekino |
| 6,747,073 | B1 | 6/2004 | Pfaff |
| 6,765,036 | B2 | 7/2004 | Dede |
| 6,852,795 | B2 | 2/2005 | Bissinger |
| 6,881,360 | B2 | 4/2005 | Stange |
| 6,899,948 | B2 | 5/2005 | Zhang |
| 6,923,420 | B2 | 8/2005 | Sekino |
| 6,933,327 | B2 | 8/2005 | Yamakawa |
| 6,984,261 | B2 | 1/2006 | Cummings |
| 7,022,173 | B2 | 4/2006 | Cummings |
| 7,137,818 | B2 | 11/2006 | Savic |
| 7,351,281 | B2 | 4/2008 | Hermansson |
| 7,368,486 | B2 | 5/2008 | Erdrich |
| 7,429,422 | B2 | 9/2008 | Davidson |
| 2002/0189405 | A1 * | 12/2002 | Liu et al. ......................... 75/767 |
| 2003/0158289 | A1 | 8/2003 | Rusin |
| 2003/0166740 | A1 | 9/2003 | Mitra |
| 2003/0181541 | A1 | 9/2003 | Wu |
| 2003/0195273 | A1 | 10/2003 | Mitra |
| 2005/0064369 | A1 | 3/2005 | Zel |
| 2005/0175552 | A1 | 8/2005 | Hoic |
| 2005/0252413 | A1 | 11/2005 | Kangas |
| 2005/0252414 | A1 | 11/2005 | Craig |
| 2005/0256223 | A1 | 11/2005 | Kolb |
| 2006/0052232 | A1 | 3/2006 | Bretscher |
| 2007/0042889 | A1 | 2/2007 | Apel |
| 2008/0200587 | A1 | 8/2008 | Filiatrault |

FOREIGN PATENT DOCUMENTS

| | | |
|---|---|---|
| DE | 3201109 | 7/1983 |
| DE | 3316852 | 11/1984 |
| DE | 19540623 | 5/1997 |
| DE | 10351885 | 5/2004 |
| EP | 094914 | 11/1983 |
| EP | 0173567 | 3/1986 |
| EP | 0184467 | 6/1986 |
| EP | 0238025 | 9/1987 |
| EP | 0373384 | 6/1990 |
| EP | 0434334 | 6/1991 |
| EP | 0530926 | 3/1993 |
| EP | 0712622 | 11/1995 |
| EP | 0712912 | 5/1996 |
| EP | 0841304 | 5/1998 |
| EP | 1229886 | 2/2000 |
| EP | 1227782 | 10/2000 |
| EP | 1051961 | 11/2000 |
| EP | 1329430 | 7/2003 |
| EP | 1400232 | 3/2004 |
| EP | 1484046 | 12/2004 |
| GB | 2310855 | 9/1997 |
| JP | 54-077776 | 6/1979 |
| JP | 50-024275 A | 3/1981 |
| JP | 58-079818 | 5/1983 |
| JP | 58-135131 | 8/1983 |
| JP | 59-107969 | 6/1984 |
| JP | 60-011407 | 1/1985 |
| JP | 60-103033 | 6/1985 |
| JP | 60-135468 | 7/1985 |
| JP | 60-137827 | 7/1985 |
| JP | 60-176920 | 9/1985 |
| JP | 60-255622 | 12/1985 |
| JP | 61-051011 | 3/1986 |
| JP | 61-141620 | 6/1986 |
| JP | 61-227917 | 10/1986 |
| JP | 61-270217 | 11/1986 |
| JP | 61-295259 | 3/1987 |
| JP | 62-065932 | 3/1987 |
| JP | 62-089701 | 4/1987 |
| JP | 62-091421 | 4/1987 |
| JP | 62-128924 | 6/1987 |
| JP | 62-212224 | 9/1987 |
| JP | 62-226815 | 10/1987 |
| JP | 63-002809 | 1/1988 |
| JP | 63-176335 | 7/1988 |
| JP | 1076919 | 3/1989 |
| JP | 1079015 | 3/1989 |
| JP | 1083518 | 3/1989 |
| JP | 1083519 | 3/1989 |
| JP | 1083520 | 3/1989 |
| JP | 1115849 | 5/1989 |
| JP | 1176225 | 7/1989 |
| JP | 2137729 | 5/1990 |
| JP | 2137730 | 5/1990 |
| JP | 2137731 | 5/1990 |
| JP | 2137732 | 5/1990 |
| JP | 346407 | 7/1991 |
| JP | 3174326 | 7/1991 |
| JP | 3258707 | 11/1991 |
| JP | 4031307 | 2/1992 |
| JP | 472768 | 3/1992 |
| JP | 4089319 | 3/1992 |
| JP | 61-57230 | 6/1994 |
| JP | 62-47825 | 9/1994 |
| JP | 7041315 | 2/1995 |
| JP | 07-081930 A | 3/1995 |
| JP | 71-18016 | 5/1995 |
| JP | 7196428 | 8/1995 |
| JP | 82-77114 | 10/1996 |
| JP | 83-11115 | 11/1996 |
| JP | 91-94674 | 7/1997 |
| JP | 92-35119 | 9/1997 |
| JP | 10306008 | 11/1998 |
| JP | 11-335220 | 12/1999 |
| JP | 2005263648 | 9/2005 |
| SU | 1018638 | 5/1983 |
| SU | 1526695 | 12/1989 |
| WO | 93/05875 | 4/1993 |
| WO | 96/34829 | 11/1996 |
| WO | 97/45377 | 12/1997 |
| WO | 98/13008 | 4/1998 |
| WO | 99/17716 | 4/1999 |
| WO | 00/03688 | 1/2000 |
| WO | 00/20494 | 4/2000 |
| WO | 00/38619 | 7/2000 |
| WO | 00/42092 | 7/2000 |
| WO | 01/07444 | 2/2001 |
| WO | 01/17482 | 3/2001 |
| WO | 01/30304 | 5/2001 |
| WO | 01/30305 | 5/2001 |
| WO | 01/30306 | 5/2001 |
| WO | 01/30307 | 5/2001 |
| WO | 03/063804 | 8/2003 |
| WO | 2004/000743 | 12/2003 |
| WO | 2004/060327 | 7/2004 |
| WO | 2005/097043 | 10/2005 |
| WO | 2007/064230 | 6/2007 |
| WO | 2007/098878 | 9/2007 |
| WO | 2007/141324 | 12/2007 |
| WO | 2008/000313 | 1/2008 |
| WO | 2008/083275 | 7/2008 |
| WO | 2010/045105 | 4/2010 |

OTHER PUBLICATIONS

ASTM D 523-89 (Reapproved 1999), "Standard Test Method for Specular Gloss" 5 pgs.

Blumenthal, "The Chemical Behavior of Zirconium," D. Van Nostrand Company, Princeton, NJ, © 1958, pp. 311-338.

Burgard, "Routes to Deagglomerated Nanopowder by Chemical Synthesis," *Materials Research Society*, Mat. Res. Soc. Symp. Proc., vol. 346, 1994, pp. 101-107.

Burgard, "Synthesis and Colloidal Processing of Nanocrystalline (Y2O3-Stabilized) ZrO2 Powders by a Surface Free Energy Con-

(56) References Cited

OTHER PUBLICATIONS trolled Process," *Materials Research Society*, Mat. Res. Soc. Symp., Proc., vol. 432, 1997, pp. 113-121.
Cabot Corporation Product Brochure, "Cab-O-Sil.RTM. Untreated Fumed Silica Properties and Functions," Title page, Publication page, and pp. 3-5 (1978).
Chatry, "The Role of Complexing Ligants in the Formation of Non-Aggregated Nanoparticles of Zirconia," Chatry , Journal of Sol-Gel Science and Technology, vol. 1, 1994, pp. 233-240.
Chen, "Synthesis of Artificial Opals with Uniform Mesoporous Silica Spheres", Chemistry Letters (2004), 33(7), pp. 838-839. [ISSN: 0366-7022].
Craig, "Direct Esthetic Restorative Materials," *Restorative Dental Materials*, 8th ed., 1989, p. 256-257.
Definition of "binary compound," Oct. 9, 1997, [retrieved on 16, 2001] Retrieved from the On-line Medical Dictionary using Internet <URL:http:/www.graylab.ac.uk/cgi-bin/omd?binary+compound>, 1 pg.
Definition of "oxide," Oct. 9, 1997, [retrieved on 16, 2001]Retrieved from the On-line Medical Dictionary using Internet <URL:http://www.graylab.ac.uk/cgi-bin/omd?oxide>, 1 pg.
Degussa AG Product Brochure, "Technical Bulletin Pigments," AEROSIL.RTM. in Pharmaceuticals and Cosmetics, No. 49, Title page, Publication page, and pp. 5 and 6, (Sep. 1997).
Degussa AG Product Brochure, Technical Bulletin Pigments, AEROSIL.RTM. as a Thickening Agent for Liquid Systems, No. 23, Title page, Publication page, and pp. 3 and 29, (Jul. 1989).
Egon Matijevic, Surface and Colloid Science, vol. 6, ed., Wiley Interscience, Potsdam, NY, 1973, pp. 23-29.
Escobedo, "Preparation of Size Controlled Nanometric Spheres of Colloidal Silica for Synthetic Opal Manufacture", Material Science Forum (2006), V509, pp. 187-192. [ISSN: 0255-5476].
Grant and Hackh's Chemical Dictionary,5th Edition, Dr. Roger Grant, Ed., Title Page, Publication Page, p. 106 and p. 231 (1987).
Gregg, "The Use of Gas Adsorption for the Determination of Surface Area and Pore Size Distribution," *Adsorption, Surface Area, and Porosity*, Brunauer-Emmet-Tell (BET) method, (Academic Press, London, 1982) pp. 283-286.
Joen, "Hydrothermal Synthesis of ER-Doped Luminescent $TiO_2$ Nanoparticles", Chem. Mater., 2003, 15(6), pp. 1256-1263.
Li, "Fabrication of $TiO_2$ Inverse Opal Film and its Application in Chemical Sensor", Huaxue Xuebao (2006), No. 14, 64, pp. 1489-1494. [ISSN: 0567-7351].
Liz-Marzán, "Three-Dimensional Assemblies of Silica-Coated Metal Nanoparticles", IPAP Conference Series 3 (2001), (Proceedings of the International Symposium on Cluster Assembled Materials, 2001), pp. 84-87.
Macosko, "Rheology Principles, Measurements, and Applications," VCH Publishers, Inc., New York, 1994, p. 92-98.
MAHR GmbH, "Perthometer, Surface Texture Parameters", Gottingen, Germany Edition, Jan. 9, 1999, p. 10.
Pramatarova, "Natural Opal as a Model System for Studying the Process of Biomineralization", Diffusion and Defect Data Pt.B: Solid State Phenomena, V106 (2005), pp. 75-78. [ISSN: 1012-0394].
Search Report of International Application No. PCT/US2007/089045, 4 pages.
Search Report of International Application No. PCT/US2009/029597, 3 pages.
Search Report of International Application No. PCT/US2009/060104, 3 pages.
Search Report of International Application No. PCT/US2000/04614, 3 pages.
Wan, "Bio-Inspired Polymer Dental Composites with Ordered Filler Arrangement", ACS Polymeric Materials: Science and Engineering. Fall Meeting 2006, 95, Polymeric Materials: Science & Engineering, pp. 583-584.
Wang, "Fabrication of Two- and Three-Dimensional Silica Nanocolloidal Particle Arrays", Journal of Physical Chemistry B (2003), 107(v 15), pp. 3400-3404.
Watts, "Determination of Polymerization Shrinkage Kinetics in Visible-Light-Cured Materials: Methods of Development," Dental Materials, Oct. 1991, pp. 281-286.
Written Opinion of International Application No. PCT/US2000/029597, 5 pages.
Written Opinion of International Application No. PCT/US2007/089045, 6 pages.
Written Opinion of International Application No. PCT/US2009/060104, 6 pages.
Written Opinion of International Application No. PCT/US2000/04614, 11 pages.
Zhang, "Monodisperse $SiO_2$ Nanospheres Prepared by Batch/Semibatch Process and Its Opals", Diffusion and Defect Data-Solid State Data, Pt. B: Solid State Pehnomena (2007), V121-123, pp. 179-182. [ISSN: 1012-0394].
Zhou, "A Novel Tailored Bimodal Porous Silica with Well-Defined Inverse Opal Microstructure and Super-Microporous Lamellar Nanostructure", Chemical Communications, Cambridge, UK, (Sep. 11, 2003), (20), 2564-2565.

* cited by examiner

DENTAL FILLER AND METHODS

CROSS REFERENCE TO RELATED APPLICATIONS

This application is a national stage filing under 35 U.S.C. 371 of PCT/US2007/089045, filed Dec. 28, 2007, which claims priority to U.S. Application No. 60/877,526 filed Dec. 28, 2006, the disclosure of which is incorporated by reference in its/their entirety herein.

FIELD OF THE INVENTION

The present invention is directed to dental fillers and methods of making dental fillers. The invention relates broadly to fillers containing inorganic oxide particles for use in dental materials.

BACKGROUND OF THE INVENTION

Dental materials generally have unique requirements as compared to the broad spectrum of composite materials. For health reasons, dental materials should be suitable for use in the oral environment. In certain instances, durability of a dental material is important to ensure satisfactory performance. For example, high strength and durability is desirable for dental work that is performed at dentition locations where mastication forces are generally great. In other instances, aesthetic character or quality is highly desired. This is often the case where dental work is performed at locations where a tooth repair or restoration can be seen from a relatively short distance.

It is also generally desired that the dental restorative material blend well with the surrounding dentition and that the dental restorative material looks life-like. Aesthetic quality in dental materials is typically achieved by creating material that has tooth-like colors/shades. Many fills, however, generally have less mechanical strength than is desired.

Radiopacity of a dental material can also be useful in dentistry. Radiopaque composites can be examined using standard dental X-ray equipment, thereby facilitating long term detection of marginal leakage or caries in tooth tissues adjacent to a cured composite.

SUMMARY OF THE INVENTION

The present invention is directed to dental fillers and methods of making dental fillers. The invention relates broadly to fillers containing inorganic oxide particles for use in dental materials and to methods of making the fillers. In particular, the present invention is directed to the use of water soluble thermally fugitive organic binders for creating friable, highly aesthetic dental fillers. The water soluble thermally fugitive organic binders typically are admixed with a metal oxide sol and dried to create a product containing at least a portion of the water soluble thermally fugitive organic binders. Subsequent calcining of the dried product creates a dental filler. The water soluble thermally fugitive organic binder is oxidized, evaporates or is otherwise removed during calcining, and thus functions as thermally fugitive organic binder. Generally, the fillers of the invention are clusters comprising a plurality of at least two amorphous, inorganic oxides: non-heavy metal oxide particles and a heavy metal oxide. The fillers mixed in a hardenable resin provide radiopaque dental materials that have high strength, good aesthetic character, and good retention of polish.

In general, implementations of the invention include a method of making a filler for dental material comprising admixing a metal oxide sol, and a water-soluble organic binder; drying said mixed sol; and calcining said dried product; wherein said filler is a cluster comprising metal oxide. In certain implementations the invention includes a method of making a filler for dental material comprising admixing a non-heavy metal oxide sol, and a water-soluble organic binder; drying said mixed sol; and calcining said dried product; wherein said filler is a cluster comprising non-heavy metal oxide. In certain implementations the invention includes a method of making a filler for dental material comprising admixing a non-heavy metal oxide sol, a heavy metal containing material, and a water-soluble organic binder; drying said mixed sol; and calcining said dried product; wherein said filler is a cluster comprising non-heavy metal oxide and a heavy metal oxide.

In certain embodiments the ratio of organic binder to heavy metal oxide-containing material is at least 0.75 to 1, in other implementations the ratio is from 0.25 to 2. Suitable organic binders include sugars, such as disaccharides, trisaccharides. A particularly useful water-soluble organic binder comprises sucrose. Another useful water-soluble organic binder comprises polyethylene glycol The invention provides fillers useful in dental materials to provide strong, highly aesthetic, radiopaque materials. Advantageously, the fillers in a hardenable resin provide dental materials that are able to retain their polish after repetitive abrasive contact. In some embodiments the filler comprises a cluster of non-heavy metal oxide particles and a heavy metal oxide, where the cluster has an average diameter of less than about 5 µm. More preferably the cluster has an average diameter of less than 2 µm. In other embodiments the filler comprises a cluster of non-heavy metal oxide particles, where the cluster has an average diameter of less than about 5 µm. More preferably the cluster has an average diameter of less than 2 µm.

The invention generally includes providing an acidic silica sol mixed with zirconyl acetate and a water-soluble organic binder, specifically a water-soluble thermally fugitive organic binder. The water is removed from this mixture, and then the mixture is heated under an oxygen-containing atmosphere at conditions designed to minimize interparticle sintering while oxidizing and/or evaporating the thermally fugitive organic binder to produce a dental filler. During the process of the invention, the water evaporates, leaving behind the binder and the silica/zirconia sol, often in the form of ceramic foam, ceramic powder, for example.

In certain embodiments the water-soluble thermally fugitive binder includes, for example, sucrose, polyvinyl alcohol, or polyethylene glycol. In certain embodiments the water soluble thermally fugitive organic binder is a disaccharide. Such disaccharides can be selected from the group comprising sucrose, lactose, and maltose. In alternative embodiments, the water soluble thermally fugitive organic binder is a trisaccharide, which is an oligosaccharide composed of three monosaccharides.

Suitable binders generally do not volatilize at temperatures below that of water, and thus generally volatilize at temperatures above about 100° C. Specifically, the water-soluble binder generally does not volatilize at temperatures below about 100° C., more desirably below about 150° C. The binder can be expected to typically oxidize at high temperatures, frequently around 175 to 200° C. or higher. Thus, it is generally desirable that the binder remain non-volatile at temperatures close to the charring temperature of the binder. It is generally desirable that the resulting nanoparticles within the cluster be as distinct as possible, and thus be loosely held together. This produces a more friable material that easily breaks down into smaller particles.

BRIEF DESCRIPTION OF THE DRAWING

The invention may be more completely understood in connection with the following drawings, in which.

Figure 1:
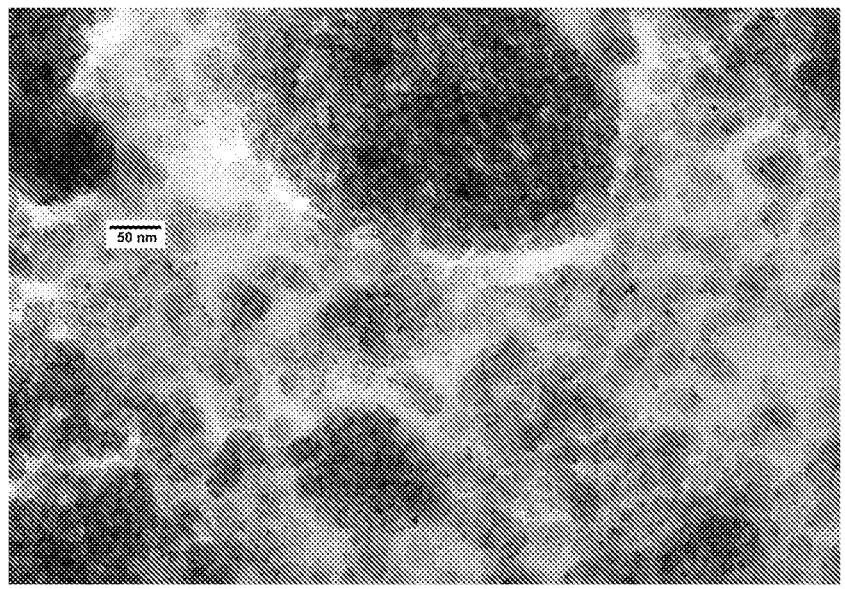
FIG. 1 is a digital image of a TEM (transmission electron micrograph) of a prior dental material.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

The present invention provides a method for producing fillers that can be loaded into a dental material to provide materials having radiopacity, high strength, high aesthetic character, and high retention of polish. High aesthetic quality is achieved by providing a dental material that possesses high translucency and good polish. Advantageously, the dental materials of the invention are also preferably able to retain their polish even after exposure to repetitive abrasion, such as through brushing with toothpaste.

The fillers of the invention can comprise a cluster of non-heavy metal oxide particles and heavy metal oxide. As explained below, the heavy metal oxide (when present) can be incorporated into the cluster as individual particles, a coating on the non-heavy metal oxide particles, or as a region in non-heavy metal oxide particles. Regardless of the form in which the heavy metal oxide is found, the cluster of non-heavy metal oxide particles and heavy metal oxide is sometimes substantially amorphous, but can in the alternative be substantially crystalline or a mixture of amorphous and crystalline oxide.

The filler of the invention can be used in dental materials such as, for example, dental adhesives, artificial crowns, anterior or posterior fillings, casting materials, cavity liners, cements, coating compositions, mill blanks, orthodontic devices, restoratives, prostheses, and sealants. In a preferred aspect, the dental material is a dental restorative. The restoratives of the invention can be placed directly in the mouth and cured (hardened) in situ, or alternatively, may be fabricated into a prosthesis outside the mouth and subsequently adhered in place inside the mouth.

Radiopacity is a very desirable property for dental composites. Radiopaque composites can be examined using standard dental X-ray equipment, thereby facilitating long term detection of marginal leakage or caries in tooth tissue adjacent to the cured composite. However, a dental composite should also have low visual opacity, that is, it should be substantially transparent or translucent to visible light. Low visual opacity is desired so that the cured dental composite will have a life-like lustre. If such a dental composite is intended to be cured or polymerized using visible light-induced photoinitiation, low visual opacity is desirable in order to reach the depth of cure required (sometimes as much as two millimeters or more), to accomplish uniform hardness in the cured composite, and to respond to the physical limitations imposed by carrying out the curing reaction within the mouth (which require, among other things, that the uncured composite usually be exposed to light from only one angle, and that the curing radiation be provided by a portable instrument).

As used herein, "hardenable" is descriptive of a material that can be cured or solidified e.g., by heating to remove solvent, heating to cause polymerization, chemical crosslinking, radiation-induced polymerization or crosslinking, or the like.

As used herein, "non-heavy metal oxide" means an oxide of elements other than those of heavy metals. In one aspect of the invention, the non-heavy metal oxide particles are silica particles.

As used herein, "heavy metal oxide" means an oxide of elements having an atomic number greater than 28. In one aspect of the invention, the heavy metal oxide is zirconium oxide.

As used herein, a "cluster" refers to the nature of the association among the non-heavy metal oxide particles present in the cluster. Typically, the non-heavy metal oxide particles are associated by relatively weak intermolecular forces that cause the non-heavy metal oxide particles to clump together, even when dispersed in a hardenable resin for a dental material. To the extent that the heavy metal oxide is present in the cluster as particles, the heavy metal oxide particles display a similar association to each other and to the non-heavy metal oxide particles.

As used herein, "substantially amorphous" means that the clusters are essentially free of crystalline structure. Absence of crystallinity (or presence of amorphous phases) is preferably determined by a procedure that provides a Crystallinity Index. The Crystallinity Index characterizes the extent a material is crystalline or amorphous, whereby a value of 1.0 is indicative of a fully crystalline structure, and a value near zero indicates presence of amorphous phase only. The fillers of the invention preferably have an index of less than about 0.1; more preferably an index of less than about 0.05.

In yet another aspect of the invention, the filler can be loaded into a hardenable resin to provide dental materials having radiopacity, low visual opacity, high mechanical strength and high aesthetic character.

The fillers of the invention can be used in dental materials such as adhesives, artificial crowns, anterior or posterior fillings, casting materials, cavity liners, cements, coating compositions, mill blanks, orthodontic devices, restoratives, prostheses, and sealants.

Method of Forming Filler

The present invention is directed to a method of making a dental material wherein a water-soluble organic binder is mixed with a non-heavy metal sol (such as an acidic silica sol) and optionally a heavy-metal containing material (such as zirconium oxide or another calcinable pressures compound). First, an aqueous sol-containing colloidal silica is mixed with a rapidly stirred sol or solution containing the desired calcinable precursor compound (e.g., zirconium acetate) and the organic binder. For some starting materials, reverse order of addition can lead to non-uniform interspersal of the amorphous and crystalline microregions in the final microparticle. The mixture preferably should be sufficiently acidic to prevent non-uniform gelation from occurring. For example, the pH preferably is below about 4.5 for a silica and zirconium acetate mixture.

The mixture can then be gelled, e.g. by raising the pH, by dehydration (using, for example, a "Rotovap" apparatus), or by heating the mixture at a temperature below its boiling point. For example, dehydration by heating below about 75° C. can be used for a silica:zirconium acetate mixture. During the drying stage and subsequent stages, the mixture will optionally be formed into a foam. The foam can increase total volume by 5, 10, 15 or more percent. In other alternatives, the mixture is not formed into a foam, but can be, for example, spray dried or directly heated without foaming or spraying.

The gel may contain a significant portion of the water or other solvents present in the starting materials, as well as air as a result of the drying. The gel is heated at a temperature and pressure sufficient to remove the water or solvents without causing boiling of the gel, e.g., for 20-24 hours at 75° C. and ambient pressure, thereby yielding a dried or substantially dried solid. This solid will typically still contain entrapped spaces as a result of the earlier foaming of the sol. The entrapped spaces promote separation of the particles resulting in looser cluster formations of less-dense particles. However, as noted above, gelling, spraying, or other methods are optional to practice of the invention, and satisfactory fillers can be formed without such gelling steps.

The solid is then heated in an oxygen-containing environment at a temperature and pressure sufficient to remove substantially all such organic compounds, e.g., in air at atmospheric pressure for 2-4 hours at 200° C. to 850° C., preferably 300° C. to 600° C. Differential thermal analysis or gravimetric analysis can be used to determine the extent of organic compound removal. The resulting powder is very friable and can be further pulverized.

The powder is next fired at a temperature and for a time sufficient to convert the precursor to polycrystalline ceramic metal oxide. The firing time and temperature should generally not be excessive, as it is desirable to retain oxide of silicon in its amorphous state, prevent the growth or formation of crystalline microregions having diameters greater than about 0.4 micrometers, and avoid densifying the microparticles to reduce the incidence of voids. During the firing cycle, the microparticles will undergo significant changes in density, surface area, pore volume and pore size. Density tends to increase during firing, while surface area and pore volume tend to decrease.

In addition to the factors already noted above, higher firing temperatures tend to increase the hardness of the microparticles and decrease water absorption. Higher firing temperatures typically also lead to faster polymerization set times for dental composites prepared from the fired microparticles.

Firing can be carried out, for example, in a muffle furnace, with the dried mixtured containing silica sol, calcinable precursor and organic binder placed in a shallow layer (e.g., 25 mm deep) in a vitreous silica boat. The fired product is then reground to provide microparticles having the desired average particle diameter, e.g., less than 50 micrometers. Regrinding can be carried out using conventional equipment and preferably employs grinding media having the same refractive index as the microparticles.

The relative molar ratio of oxide of silicon to ceramic metal oxide in the microparticles should be adjusted to provide the desired refractive index and degree of radiopacity. For $SiO_2$:$ZrO_2$ microparticles, the molar ratio of $SiO_2$ to $ZrO_2$ desirably is about 2:1 or more, with values between about 3:1 and 9:1 being preferred, and values between about 5:1 and 7.5:1 being most preferred. For microparticles containing other silica:ceramic metal oxide mixtures, the ratio of silica to ceramic metal oxide can be adjusted to provide the desired degree of radiopacity coincident with attainment of the desired refractive index and other desired physical properties in the microparticles and attainment of the desired visual opacity, durability, cure stability, and other desired physical properties in dental composites prepared therewith. The relative ratio of oxide of silicon to ceramic metal oxide can also influence polymerization set time rates for dental composites prepared therewith, with higher oxide of silicon content typically leading to faster set times.

It is sometimes desirable to avoid formation within the microparticles of crystalline microregions or inhomogeneities (e.g., voids) having diameters greater than about 0.4 micrometers, a dimension which corresponds to the shortest wavelength of visible light. The presence in the microparticles of such crystalline microregions or inhomogeneities can undesirably increase the visual opacity of a dental composite prepared therewith. Thus, in some implementations the microparticles of the present invention are formulated under conditions that substantially discourage or prevent the formation of such crystalline microregions and inhomogeneities. For brevity, such crystalline microregions and inhomogeneities will sometimes be referred to hereafter as "visually opacifying inclusions".

Prevention of visually opacifying inclusions can be achieved by filtering the silica starting material and/or ceramic metal oxide starting material through a microfine filter having a pore diameter less than 0.4 micrometers. A preferred filtration technique employs a series of progressively finer "Ballston" filters with the last filter in the series having a pore diameter less than about 0.2 to 0.25 micrometers. During subsequent processing, the gel formed by combination of the starting materials should be kept free of contaminants.

During firing of the dried and ground solid obtained from the gel, care should be taken to avoid firing temperatures and times which might promote growth of crystalline microregions to an extent sufficient to form visually opacifying inclusions, or promote reaction between the various inorganic species within the microparticles and formation of new crystalline microregions containing visually opacifying inclusions. In general, firing temperatures above about 1100° C. tend to promote formation of visually opacifying inclusions (usually as enlarged or new crystalline microregions, or as voids or cracks) and thus should be avoided.

When used in visible light-cured dental composites of the invention, the refractive index of the microparticles preferably should be matched to the refractive index of the composite resin, e.g., within about plus or minus 0.05, more preferably within about plus or minus 0.005. With currently used resins, the microparticles preferably have a refractive index less than 1.60. A preferred method for adjusting the refractive index of the microparticles is by altering the ratio of oxide of silicon to ceramic metal oxide. The microparticle refractive index can be approximately predicted by interpolation based on a comparison of the relative volume percent of silica to ceramic metal oxide (or equivalent of ceramic metal oxide if a calcinable precursor compound is employed) in the starting mixtures.

It is desirable to avoid the incorporation of fluxes which may cause melting of the microparticles during firing and formation of vitreous inclusions.

Also, the starting mixtures preferably are substantially free of chloride ion, as chloride ion may cause dental composites containing the fired microparticles to exhibit undesirable discoloration as well as reduced shelf life.

When viewed without magnification or under optical magnification, the microparticles of the invention are typically a finely divided white or off-white powder having a uniform appearance. Identification of the microstructure of such microparticles preferably is carried out using transmission electron microscopy ("TEM"). Scanning electron microscopy ("SEM") typically does not reveal the microstructure adequately, since under SEM the microparticles have a uniform greyish appearance. However, under TEM the microparticle microstructure is very distinctive and can be appreciated readily. In reference now to FIG. 1, a TEM of a prior art composition is shown. It will be observed that large zirconate clusters are surrounded by smaller microparticles of silica. In contrast, FIG. 2, a TEM of a composition made in accordance with the invention, shows well dispersed zirconate and silica microparticles.

The non-heavy metal oxide particles used in the dental materials of the invention preferably have an average diameter of less than about 100 nm; more preferably, the particles are less than about 50 nm in average diameter. These measurements are preferably based on a TEM (transmission electron microscopy) method, whereby a population of particles such as what is show in FIG. 1, is analyzed to obtain an average particle diameter. A preferred method for measuring the particle diameter is set out below, in the Test Methods section. The non-heavy metal particles used in the dental materials of the present invention are preferably substantially spherical and substantially non-porous. Although the silica is preferably essentially pure, it may contain small amounts of stabilizing ion such as ammonium and nitrate, optionally along with trace amounts of other ions, such as alkaline metal oxides.

It has been found that loading a dental material with fillers that are substantially amorphous and comprised of nano-sized particles of a non-heavy metal oxide and a heavy metal oxide imparts a combination of radiopacity and desirable levels of strength, translucency and polish. Placing the fillers of the invention in a hardenable resin provide dental materials that have exceptional capability of retaining their polish, even after being subjected to extended and repetitive abrasion, i.e. tooth brushing.

Figure 2:
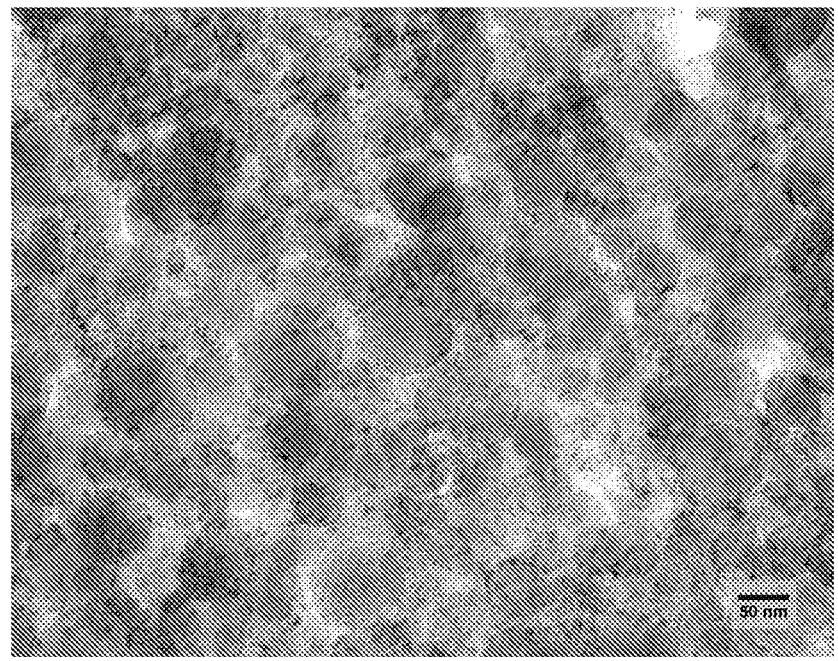
FIG. 2 is a digital image of a TEM (transmission electron micrograph) of a dental material made in accordance with the invention.

The fillers resulting from the method of the invention are weakly-bound aggregates or clusters of discrete primary particles which are clustered together as seen in FIG. 2, a TEM of the materials of the invention.

The dental material typically demonstrates significant strength. Strength can be characterized by mechanical measurements such as compressive strength and diametral tensile strength. High compressive strength in a dental material is advantageous due to the forces exerted by mastication on dental repairs, replacements and restorations. Diametral tensile strength indicates the dental material's ability to withstand compression forces that introduce a tensile stress in the material. The dental materials of the invention preferably have a compressive strength of at least about 20 MPa; more preferably, the materials have a compressive strength of at least about 200 MPa; most preferably, the materials have a compressive strength of at least about 350 MPa. Hardened dental materials of the invention preferably have a diametral tensile strength of at least about 15 MPa; more preferably at least about 40 MPa; most preferably at least about 60 MPa.

The aesthetic quality of a dental material, although a somewhat subjective characteristic, can be preferably quantified in one aspect by a visual opacity measurement. Visual opacity is indicative of dental material's level of translucency—low visual opacity is desired so that the hardened dental material will have a life-like luster. The dental materials of the present invention preferably have a Macbeth optical density of about 0.05 to 0.5; more preferably about 0.05 to 0.35; most preferably about 0.05 to 0.25.

Polishability of a dental material also contributes to the aesthetic character and quality of the material. The ability of a dental material to have a glossy finish and life-like luster upon polishing is highly desirable. An even greater benefit is the ability of a hardened material to retain its luster even after repetitive abrasive contact, such as tooth brushing. Materials of the present invention, when made in the preferred embodiment of a dental restorative, have high polishability and are able to retain the polish and luster after repetitive tooth brushing.

To evaluate a hardened, polished dental material's ability to retain its polish, a surface roughness measurement can preferably be determined by subjecting the material to a Toothbrush Abrasion Resistance Test. Using a surface roughness analyzer, commonly referred to as a surface profilometer, the material's roughness (or smoothness) after the Toothbrush Abrasion Resistance Test can be measured. A preferred apparatus to obtain the surface roughness is the WYKO RST PLUS Surface Profiling System (WYKO Corporation, Tuscon, Ariz.), using the test procedure described below in the Test Methods. The surface roughness measurement provides the average variation within the surface by measuring the average height of the profile above and below a central line. After subjecting the dental materials of the invention to the Toothbrush Abrasion Resistance Test, the dental materials preferably have a surface roughness of less than about 0.2 μm; more preferably less than about 0.15 μm.

Materials of the invention preferably possess good rheological properties. These properties as well as strength can be enhanced by using surface-modifying agents to treat the surface of the particles. Surface treatment (surface-modification) enhances the dispersibility of the particles and their ability to bind into the matrix.

The filler of the invention can be combined with a polymerizable resin to create a dental composite. Polymerizable resins suitable for use in the dental composites of the present invention are hardenable organic resins having sufficient strength, hydrolytic stability, and non-toxicity to render them suitable for use in the oral environment.

Examples of such resins include acrylate, methacrylate, urethane, and epoxy resins, e.g., those shown in U.S. Pat. Nos. 3,066,112, 3,539,533, 3,629,187, 3,709,866, 3,751,399, 3,766,132, 3,860,556, 4,002,669, 4,115,346, 4,259,117, 4,292,029, 4,308,190, 4,327,014, 4,379,695, 4,387,240 and 4,404,150, and mixtures and derivatives thereof.

A preferred polymerizable resin for use in the present invention is a mixture of diglycidylmethacrylate of Bisphenol A (frequently referred to as "BIS-GMA") and triethyleneglycol dimethacrylate (frequently referred to as "TEGDMA").

Practitioners generally desire good handling properties in a dental material, as it often translates to time savings. For example, in dental restorative work, it is desirable that dental materials do not slump because after a practitioner places the material in the mouth and manipulates the material by contouring and feathering, the practitioner generally wants the imparted shape to remain unchanged until the material is hardened.

Materials used for restorative work, having a sufficiently high yield stress, generally will not slump; that is, they will not flow under the stress of gravity.

"Contouring" refers to the process of shaping a material (using dental instruments) so that it resembles the natural dental anatomy. For easy contouring, materials should have a sufficiently high viscosity that they maintain their shape after manipulation with a dental instrument, and yet the viscosity should not be so high that it is difficult to shape the material. "Feathering" refers to the process of reducing the dental material to a thin film in order to blend the material into the natural dentition. This is done with a dental instrument at the margin of the manipulated material and the natural dentition.

It is also desirable that the dental material not stick to placement instruments, to minimize further alteration of the shape or surface topography.

In a preferred embodiment where the dental material of the invention is a restorative, the dental material preferably has little to no slump, yet easily adapts to, for example, a cavity preparation, and is easily contoured and feathered. Preferably, the dental materials of the invention do not stick to placement instruments, and are advantageously, overall, fast and easy to use in dental procedures such as, for example, restoring tooth structure.

The fillers of the invention are typically not fully densified. The term "fully dense," as used herein, is descriptive of a particle that is near theoretical density, having substantially no open porosity detectable by standard analytical techniques such as the B.E.T. nitrogen technique (based upon adsorption of $N_2$ molecules from a gas with which a specimen is contacted). Such measurements yield data on the surface area per unit weight of a sample (e.g. $m^2/g$) which can be compared to the surface area per unit weight for a mass of perfect microspheres of the same size to detect open porosity. Such measurements may be made on a Quantasorb apparatus made by Quantachrome Corporation of Syossett, N.Y. Density measurements may be made using an air, helium or water pycnometer.

A preferred method for preparing the microparticles of the present invention, referred to herein as a "sol-gel" method, involves the combining of (1) an aqueous or organic dispersion or sol of amorphous silica with (2) an aqueous or organic dispersion, sol, or solution of the desired radiopacifying ceramic metal oxide or a precursor organic or inorganic compound which is calcinable to the desired radiopacifying ceramic metal oxide; and (3) a water soluble thermally fugitive organic binder material. For brevity, the aforementioned dispersion or sol of silica will be sometimes referred to hereafter as the "silica starting material", and the aforementioned dispersion, sol, or solution of the radiopacifying ceramic metal oxide or precursor compound will sometimes be referred to hereafter as the "ceramic metal oxide starting material". The mixture of silica starting material and ceramic metal oxide starting material is dried to a solid, ground, fired, and reground to form microparticles of the invention. The microparticles can then be combined with an appropriate resin to form a composite of the invention.

Although either aqueous or organic silica starting materials can be employed in the sol-gel method, aqueous silica starting materials are preferred for reasons of economy. Suitable aqueous silica starting materials preferably contain colloidal silica at concentrations of about 1 to 50 weight percent, more preferably 15 to 35 weight percent. Suitable organic silica starting materials include organosols containing colloidal dispersions of silica in organic solvents (preferably water-miscible polar organic solvents) such as ethanol, normal or isopropyl alcohol, ethylene glycol, dimethylformamide and the various "Cellosolve" glycol ethers. The size of the colloidal silica particles in the silica starting material can vary, e.g., from 0.001 to 0.1 micrometers, preferably about 0.002 to 0.05 micrometers.

Preferred silica starting materials which can be used in this invention include aqueous sols sold under the trademark "Ludox" from E.I. DuPont de Nemours and Co. Other useful silica starting materials include dispersions or aquasols sold under the trademarks "Nalco", "Syton" and "Nyacol".

Additional suitable commercially available silica starting materials are listed in said U.S. Pat. Nos. 3,709,706 and 3,793,041.

Suitable calcinable precursor compounds preferably are carboxylates (e.g., acetates, formates, oxalates, lactates, propylates, citrates, or acetylacetonates) or salts of mineral acids (e.g., nitrates or carbonates), selection of particular precursor compounds being dictated by availability and ease of handling. Use of precursor compounds, which might form precipitates or undesired crystalline microregions prior to gellation, or form water- or acid-soluble compounds or colored impurities in the microparticles, preferably should be avoided. Representative precursor compounds useful in the present invention include zirconium acetate, barium acetate, lanthanum nitrate, strontium nitrate, and tantalum nitrate.

Other metal oxides which may not themselves provide sufficient radiopacity can, if desired, be included in the microparticles of the present invention. Such other metal oxides can be useful, for example, to adjust various physical properties of the microparticles (e.g., refractive index, hardness, density or porosity) or physical properties of dental composites prepared therewith (e.g., viscosity before cure, or compressive strength, tensile strength, or visual opacity after cure). Such other metal oxides include $Al_2O_3$ and CaO. When the above-described sol-gel method of preparation is employed, such other metal oxides can be introduced into the final microparticles by combining a dispersion or sol containing the desired other metal oxide (or a suitable dispersion or sol containing a precursor compound calcinable thereto) with the silica starting material and ceramic metal oxide starting material.

Preferred nano-sized silicas are commercially available from Nalco Chemical Co. (Naperville, Ill.) under the product designation NALCO COLLOIDAL SILICAS. For example, preferred silica particles can be obtained from using NALCO products 1040, 1042, 1050, 1060, 2327 and 2329.

In certain implementations, incorporation of the fillers into the resin can be facilitated by surface treating the fillers. Surface treatment enhances stabilization of the fillers in the hardenable resin to provide a stable dispersion of the filler in the resin. "Stable", as used herein, means a dental material in which the fillers do not settle or agglomerate after standing for a period of time, such as about 24 hours, under standard ambient conditions—e.g. room temperature (about 20-22° C.), atmospheric pressure, and no extreme electro-magnetic forces. Preferably, the surface-treatment stabilizes the filler so that they will be well dispersed in the hardenable resin and results in a substantially homogeneous composition. Furthermore, it is preferred that the filler be modified over at least a portion of its surface with a surface treatment agent so that the stabilized particle can copolymerize or otherwise react with the hardenable resin during curing. The fillers of the present invention may be treated with a resin-compatibilizing surface treatment agent. Suitable surface treatment or surface modifying agents include silane treatment agents capable of polymerizing with a resin. Suitable silane treatment agents include γ-methacryloxylpropyltrimethoxysilane, available commercially under the trade designation A-174, available commercially from Witco OSi Specialties (Danbury, Conn.) and γ-glycidoxypropyltrimethoxy silane, a product available under the trade designation G6720, available from United Chemical Technologies (Bristol, Pa.).

Alternatively a combination of surface modifying agents can be useful, wherein at least one of the agents has a functional group co-polymerizable with a hardenable resin. For example, the polymerizing group can be ethylenically unsaturated or a cyclic function subject to ring opening polymerization. An ethylenically unsaturated polymerizing group can be, for example, an acrylate or methacrylate, or vinyl group. A cyclic function subject to ring opening polymerization generally contains a heteroatom such as oxygen, sulfur or nitrogen, and preferably is a 3-membered ring containing oxygen such as an epoxide. Other surface modifying agents which do not generally react with hardenable resins can be included to enhance dispersibility or rheological properties. Examples of silane of this type include, for example, aryl polyethers, alkyl, hydroxy alkyl, hydroxy aryl, or amino alkyl functional silanes.

To achieve good translucency, it is desirable to minimize the scattering of light as it passes through the material. This is preferably accomplished by matching the average refractive index of the filler and the resin. The resins useful for the dental materials of the invention are preferably and generally thermosetting resins capable of being hardened to form a polymer network such as, for example, acrylate resins, methacrylate resins, epoxy resins, vinyl resins or mixtures thereof. Preferably, the hardenable resin is made from one or more matrix-forming oligomer, monomer, or polymer, or blends thereof.

In a preferred embodiment where the dental material of the invention is a dental composite, polymerizable resins suitable for use include hardenable organic resins having sufficient strength, hydrolytic stability, and non-toxicity to render them suitable for use in the oral environment. Examples of such resins include acrylate, methacrylate, urethane, carbamoylsiocyanurate and epoxy resins, e.g., those shown in U.S. Pat. Nos. 3,066,112, 3,539,533, 3,629,187, 3,709,866, 3,751,399, 3,766,132, 3,860,556, 4,002,669, 4,115,346, 4,259,117, 4,292,029, 4,308,190, 4,327,014, 4,379,695, 4,387,240 and 4,404,150, and mixtures and derivatives thereof.

One class of suitable hardenable resins are materials having free radically active functional groups and include monomers, oligomers, and polymers having one or more ethylenically unsaturated groups. Alternatively, the hardenable resin can be a material from the class of resins that include cationically active functional groups. In another alternative, a mixture of hardenable resins that include both cationically curable and free radically curable resins may be used for the dental materials of the invention.

In the class of hardenable resins having free radically active functional groups, suitable materials for use in the invention contain at least one ethylenically unsaturated bond, and are capable of undergoing addition polymerization. Such free radically polymerizable materials include mono-, di- or polyacrylates and methacrylates such as methyl acrylate, methyl methacrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, the diglycidyl methacrylate of bis-phenol A ("Bis-GMA"), bis[1-(2-acryloxy)]-p-ethoxyphenyldimethylmethane, bis[1-(3-acryloxy-2-hydroxy)]-p-propoxyphenyldimethylmethane, and trishydroxyethyl-isocyanurate trimethacrylate; the bis-acrylates and bis-methacrylates of polyethylene glycols of molecular weight 200-500, copolymerizable mixtures of acrylated monomers such as those in U.S. Pat. No. 4,652,274, and acrylated oligomers such as those of U.S. Pat. No. 4,642,126; and vinyl compounds such as styrene, diallyl phthalate, divinyl succinate, divinyl adipate and divinylphthalate. Mixtures of two or more of these free radically polymerizable materials can be used if desired.

For free radical polymerization (hardening), an initiation system can be selected from systems which initiate polymerization via radiation, heat, or redox/auto-cure chemical reaction. A class of initiators capable of initiating polymerization of free radically active functional groups includes free radical-generating photoinitiators, optionally combined with a photosensitizer or accelerator. Such initiators typically can be capable of generating free radicals for addition polymerization upon exposure to light energy having a wavelength between 200 and 800 nm.

A variety of visible or near-IR photoinitiator systems may be used for photopolymerization of free-radically polymerizable materials useful in the invention. For example, in free radical polymerization (hardening), a photoinitiation system can be selected from systems which initiate polymerization via a two component system of an amine and an α-diketone as described in U.S. Pat. No. 4,071,424, which is herein incorporated by reference. Alternatively, the resin can be combined with a three component or ternary photoinitiator system such as described in U.S. Pat. No. 5,545,676 which is incorporated herein by reference.

In the ternary photoinitator system, the first component is an iodonium salt, i.e., a diaryliodonium salt. The iodonium salt is preferably soluble in the monomer and shelf-stable (i.e., does not spontaneously promote polymerization) when dissolved therein in the presence of the sensitizer and donor. Accordingly, selection of a particular iodonium salt may depend to some extent upon the particular monomer, polymer or oligomer, sensitizer and donor chosen. Suitable iodonium salts are described in U.S. Pat. Nos. 3,729,313, 3,741,769, 3,808,006, 4,250,053 and 4,394,403, the iodonium salt disclosures of which are incorporated herein by reference. The iodonium salt can be a simple salt (e.g., containing an anion such as $Cl^-$, $Br^-$, $I^-$ or $C_4H_5 SO_3^-$) or a metal complex salt (e.g., containing $SbF_5 OH^-$ or $AsF_6^-$). Mixtures of iodonium salts can be used if desired. Preferred iodonium salts include diphenyliodonium salts such as diphenyliodonium chloride, diphenyliodonium hexafluorophosphate and diphenyliodonium tetrafluoroborate.

The second component in a ternary photoinitiator system is a sensitizer. The sensitizer desirably is soluble in the monomer, and is capable of light absorption somewhere within the range of wavelengths of greater than 400 to 1200 nanometers, more preferably greater than 400 to 700 nanometers and most preferably greater than 400 to about 600 nanometers. The sensitizer may also be capable of sensitizing 2-methyl-4,6-bis(trichloromethyl)-s-triazine, using the test procedure described in U.S. Pat. No. 3,729,313, which is incorporated herein by reference. Preferably, in addition to passing this test, a sensitizer is also selected based in part upon shelf stability considerations. Accordingly, selection of a particular sensitizer may depend to some extent upon the particular monomer, oligomer or polymer, iodonium salt and donor chosen.

Suitable sensitizers can include compounds in the following categories: ketones, coumarin dyes (e.g., ketocoumarins), xanthene dyes, acridine dyes, thiazole dyes, thiazine dyes, oxazine dyes, azine dyes, aminoketone dyes, porphyrins, aromatic polycyclic hydrocarbons, p-substituted aminostyryl ketone compounds, aminotriaryl methanes, merocyanines, squarylium dyes and pyridinium dyes. Ketones (e.g., monoketones or alpha-diketones), ketocoumarins, aminoarylketones and p-substituted aminostyryl ketone compounds are preferred sensitizers. For applications requiring high sensitivity, it is preferred to employ a sensitizer containing a julolidinyl moiety. For applications requiring deep cure (e.g., cure of highly-filled composites), it is preferred to employ sensitizers having an extinction coefficient below about 1000, more preferably below about 100, at the desired wavelength of irradiation for photopolymerization. Alternatively, dyes that exhibit reduction in light absorption at the excitation wavelength upon irradiation can be used.

For example, a preferred class of ketone sensitizers has the formula:

$$ACO(X)_bB$$

where X is CO or $CR^5R^6$, where $R^5$ and $R^6$ can be the same or different, and can be hydrogen, alkyl, alkaryl or aralkyl, b is zero or one, and A and B can be the same or different and can be substituted (having one or more non-interfering substituents) or unsubstituted aryl, alkyl, alkaryl, or aralkyl groups, or together A and B can form a cyclic structure which can be a substituted or unsubstituted cycloaliphatic, aromatic, heteroaromatic or fused aromatic ring.

Suitable ketones of the above formula include monoketones (b=0) such as 2,2-, 4,4- or 2,4-dihydroxybenzophenone, di-2-pyridyl ketone, di-2-furanyl ketone, di-2-thiophenyl ketone, benzoin, fluorenone, chalcone, Michler's ketone, 2-fluoro-9-fluorenone, 2-chlorothioxanthone, acetophenone, benzophenone, 1- or 2-acetonaphthone, 9-acetylanthracene, 2-, 3- or 9-acetylphenanthrene, 4-acetylbiphenyl, propiophenone, n-butyrophenone, valerophenone, 2-, 3- or 4-acetylpyridine, 3-acetylcoumarin and the like. Suitable diketones include aralkyldiketones such as anthraquinone, phenanthrenequinone, o-, m- and p-diacetylbenzene, 1,3-, 1,4-, 1,5-, 1,6-, 1,7- and 1,8-diacetylnaphthalene, 1,5-, 1,8- and 9,10-diacetylanthracene, and the like. Suitable alpha-diketones (b=1 and X=CO) include 2,3-butanedione, 2,3-pentanedione, 2,3-hexanedione, 3,4-hexanedione, 2,3-heptanedione, 3,4-heptanedione, 2,3-octanedione, 4,5-octanedione, benzil, 2,2'-3 3'- and 4,4'-dihydroxylbenzil, furil, di-3,3'-indolylethanedione, 2,3-bornanedione (camphorquinone), biacetyl, 1,2-cyclohexanedione, 1,2-naphthaquinone, acenaphthaquinone, and the like.

The third component of a ternary initiator system is a donor. Preferred donors include, for example, amines (including aminoaldehydes and aminosilanes), amides (including phosphoramides), ethers (including thioethers), ureas (including thioureas), ferrocene, sulfinic acids and their salts, salts of ferrocyanide, ascorbic acid and its salts, dithiocarbamic acid and its salts, salts of xanthates, salts of ethylene diamine tetraacetic acid and salts of tetraphenylboronic acid. The donor can be unsubstituted or substituted with one or more non-interfering substituents. Particularly preferred donors contain an electron donor atom such as a nitrogen, oxygen, phosphorus, or sulfur atom, and an abstractable hydrogen atom bonded to a carbon or silicon atom alpha to the electron donor atom. A wide variety of donors is disclosed in U.S. Pat. No. 5,545,676, which is incorporated herein by reference.

Alternatively, free-radical initiators useful in the invention include the class of acylphosphine oxides, as described in European Patent Application No. 173567, U.S. Pat. No. 4,737,593 and United Kingdom Pat No. GB 2,310,855. Such acylphosphine oxides are of the general formula $$(R^9)_2—P(=O)—C(=O)—R^{10}$$

wherein each $R^9$ individually can be a hydrocarbyl group such as alkyl, cycloalkyl, aryl, and aralkyl, any of which can be substituted with a halo-, alkyl- or alkoxy-group, or the two $R^9$ groups can be joined to form a ring along with the phosphorous atom, and wherein $R^{10}$ is a hydrocarbyl group, an S-, O-, or N-containing five- or six-membered heterocyclic group, or a —Z—C(=O)—P(=O)—$(R^9)_2$ group, wherein Z represents a divalent hydrocarbyl group such as alkylene or phenylene having from 2 to 6 carbon atoms.

Preferred acylphosphine oxides useful in the invention are those in which the $R^9$ and $R^{10}$ groups are phenyl or lower alkyl- or lower alkoxy-substituted phenyl. By "lower alkyl" and "lower alkoxy" is meant such groups having from 1 to 4 carbon atoms. Most preferably, the acylphosphine oxide is bis(2,4,6-trimethylbenzoyl)phenyl phosphine oxide (IRGACURE™ 819, Ciba Specialty Chemicals, Tarrytown, N.Y.).

Tertiary amine reducing agents may be used in combination with an acylphosphine oxide. Illustrative tertiary amines useful in the invention include ethyl 4-(N,N-dimethylamino) benzoate and N,N-dimethylaminoethyl methacrylate. The initiator can be employed in catalytically-effective amounts, such as from about 0.1 to about 5 weight percent, based on the weight of ethylenically-unsaturated compound present, of the acylphosphine oxide plus from about 0.1 to about 5 weight percent, based on the weight of ethylenically-unsaturated compound present, of the tertiary amine.

Commercially-available phosphine oxide photoinitiators capable of free-radical initiation when irradiated at wavelengths of greater than 400 nm to 1200 nm include a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE™ 1700, Ciba Specialty Chemicals), 2-benzyl-2-(N,N-dimethylamino)-1-(4-morpholinophenyl)-1-butanone (IRGACURE™ 369, Ciba Specialty Chemicals), bis($\eta^5$-2,4-cyclopentadien-1-yl)-bis(2,6-difluoro-3-(1H-pyrrol-1-yl)phenyl)titanium (IRGACURE™ 784 DC, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR™ 4265, Ciba Specialty Chemicals), and ethyl-2,4,6-trimethylbenzylphenyl phosphinate (LUCIRIN™ LR8893X, BASF Corp., Charlotte, N.C.).

Another free-radical initiator system that can alternatively be used in the dental materials of the invention includes the class of ionic dye—counterion complex initiators comprising a borate anion and a complementary cationic dye. Borate salt photoinitiators are described, for example, in U.S. Pat. Nos. 4,772,530, 4,954,414, 4,874,450, 5,055,372, and 5,057,393, the disclosures of which are incorporated herein by reference. Borate anions useful in these photoinitiators generally can be of the formula $$R^1R^2R^3R^4B^-$$

wherein $R^1$, $R^2$, $R^3$, and $R^4$ independently can be alkyl, aryl, alkaryl, allyl, aralkyl, alkenyl, alkynyl, alicyclic and saturated or unsaturated heterocyclic groups. Preferably, $R^2$, $R^3$, and $R^4$ are aryl groups and more preferably phenyl groups, and $R^1$ is an alkyl group and more preferably a secondary alkyl group.

Cationic counterions can be cationic dyes, quaternary ammonium groups, transition metal coordination complexes, and the like. Cationic dyes useful as counterions can be cationic methine, polymethine, triarylmethine, indoline, thiazine, xanthene, oxazine or acridine dyes. More specifically, the dyes may be cationic cyanine, carbocyanine, hemicyanine, rhodamine, and azomethine dyes. Specific examples of useful cationic dyes include Methylene Blue, Safranine O, and Malachite Green. Quaternary ammonium groups useful as counterions can be trimethylcetylammonium, cetylpyridinium, and tetramethylammonium. Other organophilic cations can include pyridinium, phosphonium, and sulfonium. Photosensitive transition metal coordination complexes that may be used include complexes of cobalt, ruthenium, osmium, zinc, iron, and iridium with ligands such as pyridine, 2,2'-bipyridine, 4,4'-dimethyl-2,2'-bipyridine, 1,10-phenanthroline, 3,4,7,8-tetramethylphenanthroline, 2,4,6-tri(2-pyridyl-s-triazine) and related ligands.

Yet another alternative class of initiators capable of initiating polymerization of free radically active functional groups includes conventional chemical initiator systems such as a combination of a peroxide and an amine. These initiators, which rely upon a thermal redox reaction, are often referred to as "auto-cure catalysts." They are typically supplied as two-part systems in which the reactants are stored apart from each other and then combined immediately prior to use.

Yet another alternative class of initiators capable of initiating polymerization of free radically active functional groups that are useful for the dental materials of the invention are those that include free radical-generating thermal initiators. Examples include peroxides such as, for example, benzoyl peroxide and lauryl peroxide, and azo compounds such as, for example, 2,2-azobis-isobutyronitrile (AIBN).

An alternative class of hardenable resins useful in the dental materials of the invention may include cationically active functional groups. Materials having cationically active functional groups include cationically polymerizable epoxy resins, vinyl ethers, oxetanes, spiro-orthocarbonates, spiro-orthoesters, and the like.

Preferred materials having cationically active functional groups are epoxy resins. These materials include monomeric epoxy compounds and epoxides of the polymeric type and can be aliphatic, cycloaliphatic, aromatic or heterocyclic. These materials generally have, on the average, at least 1 polymerizable epoxy group per molecule, preferably at least about 1.5 and more preferably at least about 2 polymerizable epoxy groups per molecule. The polymeric epoxides include linear polymers having terminal epoxy groups (e.g., a diglycidyl ether of a polyoxyalkylene glycol), polymers having skeletal oxirane units (e.g., polybutadiene polyepoxide), and polymers having pendent epoxy groups (e.g., a glycidyl methacrylate polymer or copolymer). The epoxides may be pure compounds or may be mixtures of compounds containing one, two, or more epoxy groups per molecule. The "average" number of epoxy groups per molecule is determined by dividing the total number of epoxy groups in the epoxy-containing material by the total number of epoxy-containing molecules present.

These epoxy-containing materials may vary from low molecular weight monomeric materials to high molecular weight polymers and may vary greatly in the nature of their backbone and substituent groups. Illustrative of permissible substituent groups include halogens, ester groups, ethers, sulfonate groups, siloxane groups, nitro groups, phosphate groups, and the like. The molecular weight of the epoxy-containing materials may vary from about 58 to about 100,000 or more.

Useful epoxy-containing materials include those which contain cyclohexane oxide groups such as epoxycyclohexanecarboxylates, typified by 3,4-epoxycyclohexylmethyl-3,4-epoxycyclohexanecarboxylate, 3,4-epoxy-2-methylcyclohexylmethyl-3,4-epoxy-2-methylcyclohexane carboxylate, and bis(3,4-epoxy-6-methylcyclohexylmethyl)adipate. For a more detailed list of useful epoxides of this nature, reference is made to the U.S. Pat. No. 3,117,099, which is incorporated herein by reference.

Still other epoxy resins contain copolymers of acrylic acid esters or glycidol such as glycidylacrylate and glycidylmethacrylate with one or more copolymerizable vinyl compounds. Examples of such copolymers are 1:1 styrene-glycidylmethacrylate, 1:1 methylmethacrylate-glycidylacrylate and a 62.5:24:13.5 methylmethacrylate-ethyl acrylate-glycidylmethacrylate. Other useful epoxy resins are well known and contain such epoxides as epichlorohydrins, alkylene oxides, e.g., propylene oxide, styrene oxide; alkenyl oxides, e.g., butadiene oxide; glycidyl esters, e.g., ethyl glycidate.

Blends of various epoxy-containing materials are also contemplated. Examples of such blends include two or more weight average molecular weight distributions of epoxy-containing compounds, such as low molecular weight (below 200), intermediate molecular weight (about 200 to 10,000) and higher molecular weight (above about 10,000). Alternatively or additionally, the epoxy resin may contain a blend of epoxy-containing materials having different chemical natures, such as aliphatic and aromatic, or functionalities, such as polar and non-polar.

There are a host of commercially available epoxy resins which can be used in this invention. In particular, epoxides which are readily available include octadecylene oxide, epichlorohydrin, styrene oxide, vinylcyclohexene oxide, glycidol, glycidyl methacrylate, diglycidyl ether of Bisphenol A (e.g., those available under the trade designations "Epon 828", "Epon 825", "Epon 1004" and "Epon 1010" from Shell Chemical Co., "DER-331", "DER-332", and "DER-334", from Dow Chemical Co.), vinylcyclohexene dioxide (e.g., "ERL-4206" from Union Carbide Corp.), 3,4-epoxycyclohexylmethyl-3,4-epoxycyclohexene carboxylate (e.g., "ERL-4221" or "CYRACURE UVR 6110" or "UVR 6105" from Union Carbide Corp.), 3,4-epoxy-6-methylcyclohexyl-methyl-3,4-epoxy-6-methyl-cyclohexene carboxylate (e.g., "ERL-4201" from Union Carbide Corp.), bis(3,4-epoxy-6-methylcyclohexylmethyl)adipate (e.g., "ERL-4289" from Union Carbide Corp.), bis(2,3-epoxycyclopentyl)ether (e.g., "ERL-0400" from Union Carbide Corp.), aliphatic epoxy modified from polypropylene glycol (e.g., "ERL-4050" and "ERL-4052" from Union Carbide Corp.), dipentene dioxide (e.g., "ERL-4269" from Union Carbide Corp.), epoxidized polybutadiene (e.g., "Oxiron 2001" from FMC Corp.), silicone resin containing epoxy functionality, flame retardant epoxy resins (e.g., "DER-580", a brominated bisphenol type epoxy resin available from Dow Chemical Co.), 1,4-butanediol diglycidyl ether of phenolformaldehyde novolak (e.g., "DEN-431" and "DEN-438" from Dow Chemical Co.), and resorcinol diglycidyl ether (e.g., "Kopoxite" from Koppers Company, Inc.), bis(3,4-epoxycyclohexyl)adipate (e.g., "ERL-4299" or "UVR-6128", from Union Carbide Corp.), 2-(3,4-epoxycyclohexyl-5,5-spiro-3,4-epoxy)cyclohexane-meta-dioxane (e.g., "ERL-4234" from Union Carbide Corp.), vinylcyclohexene monoxide 1,2-epoxyhexadecane (e.g., "UVR-6216" from Union Carbide Corp.), alkyl glycidyl ethers such as alkyl $C_8$-$C_{10}$ glycidyl ether (e.g., "HELOXY Modifier 7" from Shell Chemical Co.), alkyl $C_{12}$-$C_{14}$ glycidyl ether (e.g., "HELOXY Modifier 8" from Shell Chemical Co.), butyl glycidyl ether (e.g., HELOXY Modifier 61" from Shell Chemical Co.), cresyl glycidyl ether (e.g., "HELOXY Modifier 62" from Shell Chemical Co.), p-ter butylphenyl glycidyl ether (e.g., "HELOXY Modifier 65" from Shell Chemical Co.), polyfunctional glycidyl ethers such as diglycidyl ether of 1,4-butanediol (e.g., "HELOXY Modifier 67" from Shell Chemical Co.), diglycidyl ether of neopentyl glycol (e.g., "HELOXY Modifier 68" from Shell Chemical Co.), diglycidyl ether of cyclohexanedimethanol (e.g., "HELOXY Modifier 107" from Shell Chemical Co.), trimethylol ethane triglycidyl ether (e.g., "HELOXY Modifier 44" from Shell Chemical Co.), trimethylol propane triglycidyl ether (e.g., "HELOXY Modifier 48" from Shell Chemical Co.), polyglycidyl ether of an aliphatic polyol (e.g., "HELOXY Modifier 84" from Shell Chemical Co.), polyglycol diepoxide (e.g., "HELOXY Modifier 32" from Shell Chemical Co.), bisphenol F epoxides (e.g., "EPN-1138" or "GY-281" from Ciba- Geigy Corp.), 9,9-bis[4-(2,3-epoxypropoxy)-phenyl]fluorenone (e.g., "Epon 1079" from Shell Chemical Co.).

It is also within the scope of this invention to use one or more epoxy resins blended together. The different kinds of resins can be present in any proportion. Optionally, monohydroxy- and polyhydroxy-alcohols may be added to the curable compositions of the invention, as chain-extenders for the epoxy resin. The hydroxyl-containing material used in the present invention can be any organic material having hydroxyl functionality of at least 1, and preferably at least 2.

Preferably the hydroxyl-containing material contains two or more primary or secondary aliphatic hydroxyl groups (i.e., the hydroxyl group is bonded directly to a non-aromatic carbon atom). The hydroxyl groups can be terminally situated, or they can be pendent from a polymer or copolymer. The molecular weight of the hydroxyl-containing organic material can vary from very low (e.g., 32) to very high (e.g., one million or more). Suitable hydroxyl-containing materials can have low molecular weights, i.e., from about 32 to 200, intermediate molecular weight, i.e., from about 200 to 10,000, or high molecular weight, i.e., above about 10,000. As used herein, all molecular weights are weight average molecular weights.

The hydroxyl-containing material can optionally contain other functionalities that do not substantially interfere with cationic cure at room temperature. Thus, the hydroxyl-containing materials can be nonaromatic in nature or can contain aromatic functionality. The hydroxyl-containing material can optionally contain heteroatoms in the backbone of the molecule, such as nitrogen, oxygen, sulfur, and the like, provided that the ultimate hydroxyl-containing material does not substantially interfere with cationic cure at room temperature. The hydroxyl-containing material can, for example, be selected from naturally occurring or synthetically prepared cellulosic materials. Of course, the hydroxyl-containing material is also substantially free of groups which may be thermally or photolytically unstable; that is, the material will not decompose or liberate volatile components at temperatures below about 100° C. or in the presence of actinic light which may be encountered during the desired curing conditions for the photocopolymerizable composition. Useful hydroxyl-containing materials are described, for example, in U.S. Pat. No. 5,856,373, which is incorporated herein by reference.

The amount of hydroxyl-containing organic material used in the compositions of the invention may vary over broad ranges, depending upon factors such as the compatibility of the hydroxyl-containing material with the epoxide, the equivalent weight and functionality of the hydroxyl-containing material, the physical properties desired in the final cured composition, the desired speed of photocure, and the like.

Blends of various hydroxyl-containing materials may be useful in the dental materials of the invention. Examples of such blends include two or more molecular weight distributions of hydroxyl-containing compounds, such as low molecular weight (below 200), intermediate molecular weight (about 200 to 10,000) and higher molecular weight (above about 10,000). Alternatively or additionally, the hydroxyl-containing material can contain a blend of hydroxyl-containing materials having different chemical natures, such as aliphatic and aromatic, or functionalities, such as polar and non-polar. As an additional example, one may use mixtures of two or more poly-functional hydroxy materials or one or more mono-functional hydroxy materials with poly-functional hydroxy materials.

For hardening resins comprising cationically active functional groups, an initiation system can be selected from systems which initiate polymerization via radiation, heat, or redox/auto-cure chemical reaction. For example, epoxy polymerization may be accomplished by the use of thermal curing agents, such as anhydrides or amines. A particularly useful example of an anhydride curing agent would be cis-1,2-cyclohexanedicarboxylic anhydride.

Alternatively and preferably, initiation systems for resins comprising cationically active functional groups are those that are photoactivated. The broad class of cationic photoactive groups recognized in the catalyst and photoinitiator industries may be used in the practice of the present invention. Photoactive cationic nuclei, photoactive cationic moieties, and photoactive cationic organic compounds are art recognized classes of materials as exemplified by U.S. Pat. Nos. 4,250,311; 3,708,296; 4,069,055; 4,216,288; 5,084,586; 5,124,417; 4,985,340, 5,089,536, and 5,856,373, each of which is incorporated herein by reference.

The cationically-curable materials can be combined with a three component or ternary photoinitiator system, as described above. Three component initiator systems are also described in U.S. patent application Ser. Nos. 08/838,835, and 08/840,093, both of which are now allowed, each of which is incorporated herein by reference.

For hardening cationically curable resins, examples of useful aromatic iodonium complex salts (i.e. the first component of the ternary photoinitiator system) include: diphenyliodonium tetrafluoroborate; di(4-methylphenyl)iodonium tetrafluoroborate; phenyl-4-methylphenyliodonium tetrafluoroborate; di(4-heptylphenyl)iodonium tetrafluoroborate; di(3-nitrophenyl)iodonium hexafluorophosphate; di(4-chlorophenyl)iodonium hexafluorophosphate; di(naphthyl)iodonium tetrafluoroborate; di(4-trifluoromethylphenyl)iodonium tetrafluoroborate; diphenyliodonium hexafluorophosphate; di(4-methylphenyl)iodonium hexafluorophosphate; diphenyliodonium hexafluoroarsenate; di(4-phenoxyphenyl)iodonium tetrafluoroborate; phenyl-2-thienyliodonium hexafluorophosphate; 3,5-dimethylpyrazolyl-4-phenyliodonium hexafluorophosphate; diphenyliodonium hexafluoroantimonate; 2,2'-diphenyliodonium tetrafluoroborate; di(2,4-dichlorophenyl)iodonium hexafluorophosphate; di(4-bromophenyl)iodonium hexafluorophosphate; di(4-methoxyphenyl)iodonium hexafluorophosphate; di(3-carboxyphenyl)iodonium hexafluorophosphate; di(3-methoxycarbonylphenyl)iodonium hexafluorophosphate; di(3-methoxysulfonylphenyl)iodonium hexafluorophosphate; di(4-acetamidophenyl)iodonium hexafluorophosphate; di(2-benzothienyl)iodonium hexafluorophosphate; and diphenyliodonium hexafluoroantimonate ($DPISbF_6$).

Of the aromatic iodonium complex salts which are suitable for use in the compositions of the invention diaryliodonium hexafluorophosphate and diaryliodonium hexafluoroantimonate are among the preferred salts. These salts are preferred because, in general, they promote faster reaction, and are more soluble in inert organic solvents than are other aromatic iodonium salts of complex ions.

As mentioned above, the second and third component of the ternary photoinitiator system is a sensitizer and an electron donor, respectively. The sensitizers useful in cationic polymerization of the dental materials of the invention are those that are described above for the free-radically cured materials. Similarly, the electron donor useful for cationic polymerization of the materials of the invention include those that are described above for the free-radically cured materials. However, in the case of cationically cured materials, the electron donor preferably meets the requirements set forth in U.S. application Ser. Nos. 08/838,835, and 08/840,093, both of which are now allowed, each of which is incorporated herein by reference, and are soluble in the polymerizable composition. The donor can also be selected in consideration of other factors, such as shelf stability and the nature of the polymerizable materials, iodonium salt and sensitizer chosen. A class of donor compounds that may be useful in the inventive systems may be selected from some of the donors described in U.S. Pat. No. 5,545,676.

The donor is typically an alkyl aromatic polyether or an N-alkyl arylamino compound wherein the aryl group is substituted by one or more electron withdrawing groups. Examples of suitable electron withdrawing groups include carboxylic acid, carboxylic acid ester, ketone, aldehyde, sulfonic acid, sulfonate and nitrile groups.

A preferred group of N-alkyl arylamino donor compounds is described by the following structural formula:

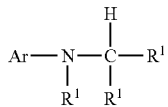

wherein each $R^1$ is independently H, $C_{1-18}$ alkyl that is optionally substituted by one or more halogen, —CN, —OH, —SH, $C_{1-18}$ alkoxy, $C_{1-18}$ alkylthio, $C_{3-18}$ cycloalkyl, aryl, COOH, COO$C_{1-18}$ alkyl, $(C_{1-18}$ alkyl$)_{0-1}$-CO—$C_{1-18}$ alkyl, $SO_3R^2$, CN or an aryl group that is optionally substituted by one or more electron withdrawing groups, or the $R^1$ groups may be joined to form a ring; and Ar is aryl that is substituted by one or more electron withdrawing groups. Suitable electron withdrawing groups include —COOH, —COO$R^2$, —$SO_3R^2$, —CN, —CO—$C_{1-18}$ alkyl and —C(O)H groups, wherein $R^2$ can be a $C_{1-18}$ straight-chain, branched, or cyclic alkyl group.

A preferred group of aryl alkyl polyethers has the following structural formula:

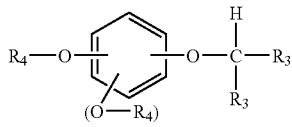

wherein n=1-3 each $R^3$ is independently H or $C_{1-18}$ alkyl that is optionally substituted by one or more halogen, —CN, —OH, —SH, $C_{1-18}$ alkoxy, $C_{1-18}$ alkylthio, $C_{3-18}$ cycloalkyl, aryl, substituted aryl, —COOH, —COO$C_{1-18}$ alkyl, —(C$_{1-18}$ alkyl)$_{0-1}$-COH, —(C$_{1-18}$ alkyl)$_{0-1}$-CO—$C_{1-18}$ alkyl, —CO—$C_{1-18}$ alkyl, —C(O)H or —$C_{2-18}$ alkenyl groups and each $R^4$ can be $C_{1-18}$ alkyl that is optionally substituted by one or more halogen, —CN, —OH, —SH, $C_{1-18}$ alkoxy, $C_{1-18}$ alkylthio, $C_{3-18}$ cycloalkyl, aryl, substituted aryl, —COOH, —COO$C_{1-18}$ alkyl, —($C_{1-18}$ alkyl)$_{0-1}$-COH, —($C_{1-18}$ alkyl)$_{0-1}$-CO—$C_{1-18}$ alkyl, —CO—$C_{1-18}$ alkyl, —C(O)H or —$C_{2-18}$ alkenyl groups.

In each of the above formulas the alkyl groups can be straight-chain or branched, and the cycloalkyl group preferably has 3 to 6 ring carbon atoms but may have additional alkyl substitution up to the specified number of carbon atoms. The aryl groups may be carbocyclic or heterocyclic aryl, but are preferably carbocyclic and more preferably phenyl rings.

Preferred donor compounds include 4-dimethylaminobenzoic acid, ethyl 4-dimethylaminobenzoate, 3-dimethylaminobenzoic acid, 4-dimethylaminobenzoin, 4-dimethylaminobenzaldehyde, 4-dimethylaminobenzonitrile and 1,2,4-trimethoxybenzene.

An alternative photoinitiator system for cationic polymerizations includes the use of organometallic complex cations essentially free of metal hydride or metal alkyl functionality selected from those described in U.S. Pat. No. 4,985,340, and such description is incorporated herein by reference and has the formula:

$$[(L^1)(L^2)M]^{+q} \quad (1)$$

wherein

M represents a metal selected from the group consisting of Cr, Mo, W, Mn, Re, Fe, Ru, Os, Co, Rh, Ir, Pd, Pt and Ni, preferably Cr, Mo, W, Mn, Fe, Ru, Co, Pd, and Ni; and most preferably Mn and Fe;

$L^1$ represents 1 or 2 cyclic, polyunsaturated ligands that can be the same or different ligand selected from the group consisting of substituted and unsubstituted cyclopentadienyl, cyclohexadienyl, and cycloheptatrienyl, cycloheptatriene, cyclooctatetraene, heterocyclic compounds and aromatic compounds selected from substituted or unsubstituted arene compounds and compounds having 2 to 4 fused rings, and units of polymers, e.g., a phenyl group of polystyrene, poly (styrene-co-butadiene), poly(styrene-co-methyl methacrylate), poly(a-methylstyrene), and the like; a cyclopentadiene group of poly(vinylcyclopentadiene); a pyridine group of poly(vinylpyridine), and the like, each capable of contributing 3 to 8 electrons to the valence shell of M;

$L^2$ represents none, or 1 to 3 nonanionic ligands contributing an even number of electrons that can be the same or different ligand selected from the group of carbon monoxide, ketones, olefins, ethers, nitrosonium, phosphines, phosphites, and related derivatives of arsenic and antimony, organonitriles, amines, alkynes, isonitriles, dinitrogen, with the proviso that the total electronic charge contributed to M results in a net residual positive charge of q to the complex;

q is an integer having a value of 1 or 2, the residual charge of the complex cation.

Organometallic salts are known in the art and can be prepared as described in, for example, EPO No. 094,914 and U.S. Pat. Nos. 5,089,536, 4,868,288, and 5,073,476, and such descriptions are incorporated herein by reference.

Examples of preferred cations include:

diphenyliodonium, ditolyliodonium, didodecylphenyliodonium, (4-octyloxyphenyl)phenyliodonium, and bis (methoxyphenyl)iodonium; triphenylsulfonium, diphenyl-4-thiophenoxyphenylsulfonium, and 1,4-phenylene-bis (diphenylsulfonium); bis($\eta^5$-cyclopentadienyl)iron(1+), bis ($\eta^5$-methylcyclopentadienyl)iron (1+), ($\eta^5$-cyclopentadienyl)($\eta^5$-methylcyclopentadienyl)iron (1+), and bis($\eta^5$-trimethylsilylcyclopentadienyl)iron (1+); bis($\eta^6$-xylenes)iron (2+), bis($\eta^6$-mesitylene)iron (2+), bis($\eta^6$-durene)iron (2+), bis($\eta^6$-pentamethylbenzene)iron (2+), and bis ($\eta^6$-dodecylbenzene) iron (2+); ($\eta^5$-cyclopentadienyl)($\eta^6$-xylenes)iron (1+), commonly abbreviated as (CpFeXy)(1+), ($\eta^5$-cyclopentadienyl)($\eta^6$-toluene)iron (1+), ($\eta^5$-cyclopentadienyl)($\eta^6$-mesitylene)iron (1+), ($\eta^5$-cyclopentadienyl)($\eta^6$-pyrene)iron (1+), ($\eta^5$-cyclopentadienyl)($\eta^6$-naphthalene) iron (1+), and ($\eta^5$-cyclopentadienyl)($\eta^6$-dodecylphenyl)iron (1+).

Alternatively, hardenable resins useful for the invention may have both cationically active and free radically active functional groups contained in a single molecule. Such molecules may be obtained, for example, by reacting a di- or poly-epoxide with one or more equivalents of an ethylenically unsaturated carboxylic acid. An example of such a material is the reaction product of UVR-6105 (available from Union Carbide) with one equivalent of methacrylic acid. Commercially available materials having epoxy and free-radically active functionalities include the "Cyclomer" series, such as Cyclomer M-100, M-101, or A-200 available from Daicel Chemical, Japan, and Ebecryl-3605 available from Radcure Specialties.

The photoinitiator compounds are preferably provided in the dental materials of the invention in an amount effective to initiate or enhance the rate of cure or hardening of the resin system. Photopolymerizable compositions useful in the invention are prepared by simply admixing, under "safe light" conditions, the components as described above. Suitable inert solvents may be employed if desired when effecting this mixture. Any solvent may be used which does not react appreciably with the components of the inventive compositions. Examples of suitable solvents include acetone, dichloromethane, and acetonitrile. A liquid material to be polymerized may be used as a solvent for another liquid or solid material to be polymerized. Solventless compositions can be prepared by simply dissolving an aromatic iodonium complex salt and sensitizer in an epoxy resin-polyol mixture with or without the use of mild heating to facilitate dissolution.

Dental materials of the invention preferably contain about 35 wt % to about 95 wt % of the fillers of the invention, based on the total weight of the hardenable resin. More preferably, the fillers are present in the dental material at concentrations of about 50 wt % to about 85 wt %.

In a preferred method of using the dental material of the invention, comprising a hardenable resin and fillers of the invention, the material is placed near or on a tooth surface, followed by a manipulation by the practitioner or laboratory to change the topography of the material, then hardening the resin. These steps can be followed sequentially or in a different order. For example, in a preferred embodiment where the dental material is a mill blank or a prosthesis, the hardening step is generally completed prior to changing the topography of the material. Changing the topography of the material can be accomplished in various ways, including manual manipulation using hand held instruments, or by machine or computer aided apparatus, such as a CAD/CAM milling machine in the case of prostheses and mill blanks. Optionally, a finishing step can be performed to polish, finish, or apply a coating on the dental material.

The following examples are given to illustrate, but not limit, the scope of this invention. Unless otherwise indicated, all parts and percentages are by weight

EXAMPLES

Unless otherwise noted, all reagents and solvents were or can be obtained from Sigma-Aldrich Corp., St. Louis Mo. Sucrose was obtained as granulated white sugar, distributed by C&H Sugar Co., Inc., Crockett, Calif.

As used herein,

"NALCO 1060" refers to a silica sol available under the trade designation NALCO 1060 from Nalco Co., Naperville, Ill.;

"10/20 ZIRCONIA SOL" refers to a zirconium oxide sol available under the trade designation "NYACOL ZR10/20" from Nyacol Nano Technologies, Inc., Ashland, Mass.;

"GF-31" refers to 3-methacryloxypropyltrimethoxysilane, available under the trade designation GENIOSIL GF 31 from Wacker Chemie AG, Munich, Germany;

"PEG-6000" refers to polyethylene glycol) having a weight average molecular weight of approximately 6000, available from Calbiochem;

"PVA" refers to polyvinyl alcohol), 86-89% hydrolyzed, having a low weight average molecular weight of approximately, available from Alfa Aesar;

"SiC" refers to silicon carbide.

Toothbrush Abrasion Resistance Test

A rectangular 20×15×3 mm thick paste of each example was cured with a dental curing light (VISILUX 2; 3M ESPE Dental Products) for 80 seconds followed by additional curing for 90 seconds in a light box (DENTACOLOR XS; Heraeus Kulzer, Inc., Armonk, N.Y.). Samples were mounted to a holder with double sided adhesive tape. The mounted examples were polished according to the following procedure, in which a series of steps were performed sequentially as shown in Table 1, using a variable speed grinder/polisher (available under the trade designation ECOMET 4 from Buehler Ltd., Lake Bluff, Ill.) with a polishing head (available under the trade designation AUTOMET 2 from Buehler, Ltd., Lake Bluff, Ill.).

TABLE 1

Polishing Steps

| Step# | Abrasive | Grit | Lubricant | RPM | Rotation | Load (lbs) per sample | Time |
|---|---|---|---|---|---|---|---|
| 1 | SiC | 320 | Water | 150 | Clockwise | 1 | 0:40 |
| 2 | Rinse | | Water | | | | |
| 3 | SiC | 600 | Water | 150 | Clockwise | 1 | 1:00 |
| 4 | Rinse | | Water | | | | |
| 5 | 9 mm diamond paste | 9 mm diamond. | Oil | 130 | Clockwise | 1 | 2:00 |
| 6 | Rinse | | Water, soapy water, isopropanol | | | | |
| 7 | 3 mm diamond paste | 3 mm diamond | Oil | 130 | Clockwise | 1 | 2:00 |
| 8 | Rinse | | Water, soapy water, isopropanol | | | | |
| 9 | Master Polish Solution | Master Polish | Water | 120 | Clockwise | 0.75 | 1:40 |
| 10 | Rinse | | Water, soapy water, isopropanol | | | | |

A micro-tri-gloss instrument (MICRO-TRI-GLOSS; BYK-Gardner, Columbia, Md.) was used to collect photoelectric measurements of light reflected from the surface of each sample, at an angle of 60°, after polishing and brushing with a toothbrush. The procedure is generally described in ASTM D 523-89 (Reapproved 1999) Standard Test Method for Specular Gloss. Each sample was brushed for a total of 2000 cycles with a toothbrush and toothpaste (ORAL B 40 medium straight toothbrush; CREST regular flavor; The Procter and Gamble Co., Cincinnati, Ohio). Each sample was brushed using the same toothbrush by a single operator using forces approximately equal to standard tooth brushing forces. One tooth brushing cycle was a forward and a back stroke. The gloss of each sample after 2000 tooth brushing cycles was measured and is reported, as indicated by the instrument, in gloss units. Higher values of gloss units mean that the sample had higher gloss.

Preparative Example 1

Preparation of a Curable Dental Resin Composition

A curable dental resin composition was prepared essentially as described in U.S. Pat. No. 6,030,606.

Preparative Example 2

Preparation of Ion-Exchanged Silica Sol

Silica sol (NALCO 1060, 400 g) was stirred for two hours with an acidic ion exchange resin (9.1 g, available under the trade designation AMBERLITE IR-120H, Rohm and Haas Co., Philadelphia, Pa.). The mixture was filtered with 75 micron nylon mesh to afford the ion exchanged silica sol.

Example 1

Preparation of a Silica-Zirconia Filler Using Sucrose

A round bottom flask was charged with the product of Preparative Example 2 (50.73 g) and 70 weight percent aqueous nitric acid (1.49 grams). The flask was swirled to mix the two charges. 10/20 ZIRCONIA SOL (46.9 grams) was then added to the flask, which was again swirled to mix the components. Sucrose (70.3 grams) was then added to the flask and was allowed to dissolve into the mixture. Some of the volatile components were removed using a rotary evaporator until 130 grams of the mixture remained in the flask. This remaining mixture was divided among plastic beakers, which were then placed in a forced air oven to dry the mixture at approximately 105° C. As the material in each beaker dried, it expanded into a foam that had a volume of at least approximately ten times the volume of the mixture in each beaker. The resultant dry mixture was calcined in a furnace at a temperature of approximately 600° C. for 8 hours with 100 SCFM air flow through the oven to remove volatile reaction products. The resultant white powder product was ground using a mortar and pestle and was sifted overnight using a polyamide screen having a mesh opening of 30 micrometers. A 10.09 gram portion of this screened white powder product was combined in a plastic jar with ethyl acetate (19.0 g), GF-31 (1.08 g), deionized water (0.17 g), 30 weight percent aqueous ammonium hydroxide (5 drops), and 2.5 weight percent aqueous ammonium fluoride (5 drops). The jar was rolled on a roller mill overnight at room temperature and then the mixture was poured into a tray in a fume hood to dry at room temperature to afford the product.

Example 2

Preparation of a Dental Composition Including Silica-Zirconia Filler

The curable dental resin of Preparative Example 1 and the silica-zirconia filler of Example 1 were combined, using a Model DAC 150 FVZ SpeedMixer (manufactured by Flack-Tek, Inc., Landrum, S.C.) at 3500 rpm in eight thirty-second mixing cycles with three to four minutes between cycles, to prepare a dental composition that was 72 weight percent silica-zirconia filler. The composition was cured as described above, and the gloss, measured after polishing and brushing, was measured as described above. The gloss value was determined to be 86 gloss units.

Examples 3-4

Preparation of Silica-Zirconia Filler Using Sucrose

A mixture of the product of Preparative Example 2 (1458.5 g), 70 weight percent aqueous nitric acid (40.6 g), zirconium acetate solution (1183.9 g, obtained from Magnesium Elektron Inc., Flemington, N.J.), and sucrose (2002.6 g) was stirred until the mixture appeared to be homogeneous. The mixture was then divided into two portions.

The first portion (Example 3) was dried using a gap drying method essentially as described in U.S. Pat. Nos. 5,980,697 and 5,694,701, with a dispersion coating thickness of about 0.9 millimeter (0.035 inch) and a residence time of approximately 1.6 minutes (heating platen temperature 143° C. and condensing platen temperature 21° C.) to afford a light brown powder. This portion was calcined in a furnace at a temperature of approximately 625° C. for 16 hours with 180 SCFM air flow through the oven to remove volatile reaction products. The resultant white powder product was ground using a mortar and pestle and was sifted overnight using a polyamide screen having a mesh opening of 30 micrometers to afford a white powder. The second portion (Example 4) was poured directly into a furnace and was calcined and sifted essentially as described for the material of Example 3 to afford a white powder.

Each of the calcined powders of Examples 3 and 4 (25 grams each) was combined in a plastic jar with ethyl acetate (30 g), GF-31 (2.5 g), deionized water (0.5 g), and 30 weight percent aqueous ammonium hydroxide (0.5 g). Each jar was rolled on a roller mill overnight at room temperature and then the mixture was poured into a tray in a fume hood to dry at room temperature to afford the products of Examples 3 and 4.

Examples 5-6

Preparation of Dental Compositions Each Including a Silica-Zirconia Filler

The curable dental resin of Preparative Example 1 and the silica-zirconia filler of each of Examples 3 and 4 were combined, using a Model DAC 150 FVZ SpeedMixer (manufactured by FlackTek, Inc., Landrum, S.C.) at 3500 rpm in eight thirty-second mixing cycles with three to four minutes between cycles, to prepare the dental compositions of Examples 5 and 6, respectively, each of which was 72 weight percent silica-zirconia filler. Each composition was cured as described above, and the gloss, measured after polishing and brushing each sample, was measured as described above. The gloss values were determined to be 87 gloss units (Example 5) and 82 gloss units (Example 6).

Examples 7-10

Preparation of Silica-Zirconia Fillers Using Different Relative Amounts of Sucrose The silica-zirconia fillers of Examples 7-10 were prepared essentially as described in Example 4, using the amounts of materials given in Table 2. Each of the dry powders was then treated with GF-31 essentially as described in Example 4 to afford the products.

TABLE 2

The Compositions for Examples 7-10

| Example | Wt. Preparative Example 2 | Wt. 70 wt % nitric acid | Wt. Zirconium acetate solution | Wt. Sucrose |
|---|---|---|---|---|
| 7 | 145.84 g | 4.04 g | 118.38 g | 75.25 g |
| 8 | 145.8 g | 4.04 g | 118.38 g | 100.11 g |
| 9 | 145.85 g | 4.02 g | 118.36 g | 126.36 g |
| 10 | 145.84 g | 4.05 g | 118.39 g | 150.23 g |

Examples 11-14

Preparation of Dental Compositions Each Including a Silica-Zirconia Filler

The curable dental resin of Preparative Example 1 and the silica-zirconia filler of each of Examples 7-10 were combined, using a Model DAC 150 FVZ SpeedMixer (manufactured by FlackTek, Inc., Landrum, S.C.) at 3500 rpm in eight thirty-second mixing cycles with three to four minutes between cycles, to prepare the dental compositions of Examples 11-14, respectively, each of which was 72 weight percent silica-zirconia filler. Each composition was cured as described above, and the gloss, measured after polishing and brushing each sample, was measured as described above. The gloss values were determined to be 64 gloss units (Example 11), 81 gloss units (Example 12), 79 gloss units (Example 13), and 84 gloss units (Example 14).

Example 15

Preparation of Silica-Zirconia Filler Using Spray Drying

A mixture of the product of Preparative Example 2 (510.6 g), 70 weight percent aqueous nitric acid (13.7 g), zirconium acetate solution (414.8 g, obtained from Magnesium Elektron Inc., Flemington, N.J.), deionized water (923.2 g), and sucrose (350.2 g) was stirred until the mixture appeared to be homogeneous. The mixture was then spray dried using a 3-foot Niro Spray Drier (Niro 3-foot Mobile Minor™ Spray Drier, Columbia, Md.) at 240° C. inlet temperature and 80°-85° C. outlet temperature at approximately 50,000 rpm to afford a powder. The powder was then calcined, sifted, and then treated with GF-31 essentially as described in Examples 3 and 4 to afford the product.

Comparative Example 1

Spray Dried Silica-Zirconia Filler Prepared without Sucrose

A mixture of the product of Preparative Example 2 (307.5 g), 70 weight percent aqueous nitric acid (8.9 g), zirconium acetate solution (249.6 g, obtained from Magnesium Elektron Inc., Flemington, N.J.), and deionized water (557.4 g) was stirred until the mixture appeared to be homogeneous. The mixture was then spray dried and the product was calcined, sifted, and then treated with GF-31, essentially as described in Example 15, to afford the product.

Example 16

Dental Composition Including a Spray Dried Silica-Zirconia Filler

The curable dental resin of Preparative Example 1 and the silica-zirconia filler of Example 15 (spray dried; made using sucrose) were combined, using a Model DAC 150 FVZ SpeedMixer (manufactured by FlackTek, Inc., Landrum, S.C.) at 3500 rpm in eight thirty-second mixing cycles with three to four minutes between cycles, to prepare a dental composition that was 71 weight percent silica-zirconia filler. The composition was cured as described above, and the gloss, measured after polishing and brushing, was measured as described above. The gloss value was determined to be 72 gloss units.

Comparative Example 2

Dental Composition Including a Spray Dried Silica-Zirconia Filler

The curable dental resin of Preparative Example 1 and the silica-zirconia filler of Comparative Example 1 (spray dried; made without sucrose) were combined, using a Model DAC 150 FVZ SpeedMixer (manufactured by FlackTek, Inc., Landrum, S.C.) at 3500 rpm in eight thirty-second mixing cycles with three to four minutes between cycles, to prepare a dental composition that was 62 weight percent silica-zirconia filler. The composition was cured as described above, and the gloss, measured after polishing and brushing, was measured as described above. The gloss value was determined to be 53 gloss units.

Example 17

Preparation of Silica-Zirconia Filler Using PEG-6000

A round bottom flask was charged with the product of Preparative Example 2 (145.9 g) and 70 weight percent aqueous nitric acid (4.15 g). The flask was swirled to mix the two charges. Zirconium acetate solution (118.5 g, obtained from Magnesium Elektron Inc., Flemington, N.J.) was then added to the flask, which was again swirled to mix the components. PEG-6000 (150 g) was then added to the flask and was allowed to dissolve into the mixture. The resultant mixture was calcined in a furnace at a temperature of approximately 625° C. for approximately 16 hours with 150-200 SCFM air flow through the oven to remove volatile reaction products. The resultant product was ground using a mortar and pestle and was sifted overnight using a polyamide screen having a mesh opening of 30 micrometers. A 25 gram portion of this screened white powder product was combined in a plastic jar with ethyl acetate (30 g), GF-31 (2.5 g), deionized water (0.5 g), and 30 weight percent aqueous ammonium hydroxide (0.5 g). The jar was rolled on a roller mill overnight at room temperature and then the mixture was poured into a tray in a fume hood to dry at room temperature to afford the product.

Example 18

Preparation of Silica-Zirconia Filler Using PVA

A silica-zirconia filler was prepared essentially as described in Example 17, except that PVA (150 g) was used instead of PEG-6000.

Examples 19-20

Preparation of Dental Compositions Each Including a Silica-Zirconia Filler

The curable dental resin of Preparative Example 1 and the silica-zirconia filler of each of Examples 17 and 18 were combined, using a Model DAC 150 FVZ SpeedMixer (manufactured by FlackTek, Inc., Landrum, S.C.) at 3500 rpm in eight thirty-second mixing cycles with three to four minutes between cycles, to prepare the dental compositions of Examples 19 and 20, respectively, each of which was 72 weight percent silica-zirconia filler. Each composition was cured as described above, and the gloss, measured after polishing and brushing each sample, was measured as described above. The gloss values were determined to be 85 gloss units (Example 19) and 66 gloss units (Example 20).

While the present invention has been described with reference to several particular implementations, those skilled in the art will recognize that many changes may be made hereto without departing from the spirit and scope of the present invention.

The invention claimed is:

1. A method of making a filler for dental material comprising:
   a) admixing a non-heavy metal oxide sol, a heavy metal oxide-containing material, and a thermally fugitive water-soluble organic binder to form a mixed sol;
   b) drying said mixed sol into a dried product;
   c) heating the dried product in an oxygen-containing environment at a temperature sufficient to remove substantially all of the thermally fugitive water-soluble organic binder, to form a friable powder; and
   d) calcining the friable powder to form the filler as a powder;
   wherein said filler comprises a substantially amorphous cluster of non-heavy metal oxide particles and a heavy metal oxide.

2. The method of making a filler of claim 1, wherein the ratio of organic binder to heavy metal oxide-containing material is 0.25 to 2.

3. The method of making a filler of claim 1, wherein the ratio of organic binder to heavy metal oxide-containing material is 0.75 to 1.

4. The method of making a filler of claim 1, wherein the water-soluble organic binder comprises a sugar.

5. The method of making a filler of claim 1, wherein the water-soluble organic binder comprises a disaccharide.

6. The method of making a filler of claim 1, wherein the water-soluble organic binder comprises a trisaccharide.

7. The method of making a filler of claim 1, wherein the water-soluble organic binder comprises sucrose.

8. The method of making a filler of claim 1, wherein the water-soluble organic binder comprises polyethylene glycol.

9. The method of making a filler of claim 1, wherein the water-soluble organic binder comprises poly(vinyl alcohol).

10. The method of making a filler of claim 8, wherein upon the drying of said mixed sol into a dried product, the mixed sol becomes a foam wherein the foam expands by at least 10 percent.

11. The method according to claim 1, further comprising the step of surface modifying the filler.

12. The method according to claim 1, further comprising the step of admixing the filler with a hardenable resin.

* * * * *

UNITED STATES PATENT AND TRADEMARK OFFICE
CERTIFICATE OF CORRECTION

PATENT NO. : 8,647,426 B2  Page 1 of 2
APPLICATION NO. : 12/519393
DATED : February 11, 2014
INVENTOR(S) : Bradley Craig It is certified that error appears in the above-identified patent and that said Letters Patent is hereby corrected as shown below:

On Title Page 4, Column 1 (Other Publications)
Line 6, Delete "Ligants" and insert -- Ligands --, therefor.
Line 36, Delete "Emmet" and insert -- Emmett --, therefor.

On Title Page 4, Column 2 (Other Publications)
Line 40, Delete "Pehnomena" and insert -- Phenomena --, therefor.

In the Specification:

Column 2
Line 24, After "glycol" insert -- . --.

Column 6
Line 17-18, Delete "inhomogeneties" and insert -- inhomogeneities --, therefor.

Column 8
Line 16-17, Delete "Tuscon," and insert -- Tucson, --, therefor.

Column 9
Line 24, Delete "Syossett," and insert -- Syosset, --, therefor.

Column 10
Line 7-8, Delete "gellation," and insert -- gelation, --, therefor.
Line 53, Delete "methacryloxylpropyltrimethoxysilane," and insert
-- methacryloxypropyltrimethoxysilane, --, therefor.

Column 11
Line 23-24, Delete "carbamoylsiocyanurate" and insert -- carbamoylisocyanurate --, therefor.

Signed and Sealed this
Twenty-fourth Day of June, 2014

Michelle K. Lee
*Deputy Director of the United States Patent and Trademark Office*

Column 12
Line 19, Delete "photoinitator" and insert -- photoinitiator --, therefor.
Line 31, Delete "$C_4H_5SO_3^-$)" and insert -- $C_4H_5SO_3^-$) --, therefor.
Line 32, Delete "$SbF_5OH$"" and insert -- $SbF_5OH^-$ --, therefor.

Column 13
Line 32, Delete "2,2'-3 3'-" and insert -- 2,2',-3,3'- --, therefor.
Line 34, Delete "naphthaquinone," and insert -- naphthoquinone, --, therefor.
Line 34-35, Delete "acenaphthaquinone," and insert -- acenaphthoquinone, --, therefor.

Column 14
Line 57, Delete "Safranine" and insert -- Safranin --, therefor.

Column 16
Line 53, Delete "p-ter" and insert -- p-tert --, therefor.

Column 19
Line 51, Delete "—($Cl_{1-18}$ alkyl$)_{0-1}$" and insert -- —($C_{1-18}$ alkyl$)_{0-1}$ --, therefor.

Column 20
Line 49, Delete "cyclopentadienyl)iron(1+)," and insert -- cyclopentadienyl)iron (1+), --, therefor.
Line 55, Delete "dodecylbenzene) iron" and insert -- dodecylbenzene)iron --, therefor.

Column 22
Line 3, After "weight" insert -- . --.
Line 20, Delete "polyethylene" and insert -- poly(ethylene --, therefor.
Line 23, Delete "polyvinyl" and insert -- poly(vinyl --, therefor.

Column 23
Line 23, Delete "120H," and insert -- 120 H, --, therefor.

Column 25
Line 48, Delete "Drier" and insert -- Dryer --, therefor.
Line 49, Delete "Drier," and insert -- Dryer, --, therefor.